United States Patent [19]

Levy et al.

[11] Patent Number: 5,283,255

[45] Date of Patent: * Feb. 1, 1994

[54] WAVELENGTH-SPECIFIC CYTOTOXIC AGENTS

[75] Inventors: Julia G. Levy; David Dolphin; Jack J. Chow; Ethan Sternberg, all of Vancouver, Canada

[73] Assignee: The University of British Columbia, Vancouver, Canada

[*] Notice: The portion of the term of this patent subsequent to Nov. 28, 2006 has been disclaimed.

[21] Appl. No.: 943,895

[22] Filed: Sep. 11, 1992

Related U.S. Application Data

[60] Division of Ser. No. 718,393, Jun. 20, 1991, Pat. No. 5,171,749, which is a continuation-in-part of Ser. No. 414,201, Sep. 28, 1989, Pat. No. 5,095,030, which is a continuation-in-part of Ser. No. 221,161, Jul. 19, 1988, Pat. No. 4,920,143, which is a continuation-in-part of Ser. No. 41,680, Apr. 23, 1987, Pat. No. 4,883,790, which is a continuation-in-part of Ser. No. 5,204, Jan. 20, 1987, abandoned.

[51] Int. Cl.$^5$ .............................................. A61K 31/40
[52] U.S. Cl. ...................................... 514/410; 424/9; 540/145
[58] Field of Search ............... 540/145; 514/410, 185; 424/9

[56] References Cited

U.S. PATENT DOCUMENTS 4,649,151 3/1987 Dougherty et al. ............... 514/410
4,883,790 11/1989 Levy et al. ......................... 540/145

Primary Examiner—Richard L. Raymond
Attorney, Agent, or Firm—Morrison & Foerster

[57] ABSTRACT

A group of hydro-monobenzoporphyrins "green porphyrins" (Gp) having absorption maxima in the range of 670–780 nanometers is useful in treating disorders or conditions which are subject to hematoporphyrin derivative (HPD) treatment in the presence of light, or in treating virus, cells and tissues generally to destroy unwanted targets. The use of the Gp of the invention permits the irradiation for therapy to use wavelengths other than those absorbed by blood. The Gp of the invention may also be conjugated to ligands specific for receptor or to specific immunoglobulins or fragments thereof to target specific tissues or cells for the radiation treatment. Use of these materials permits lower levels of drug to be used, thus preventing side reactions which might destroy normal tissues.

26 Claims, 10 Drawing Sheets

BPD-DA

BPD-DB

BPD-MA

BPD-MB

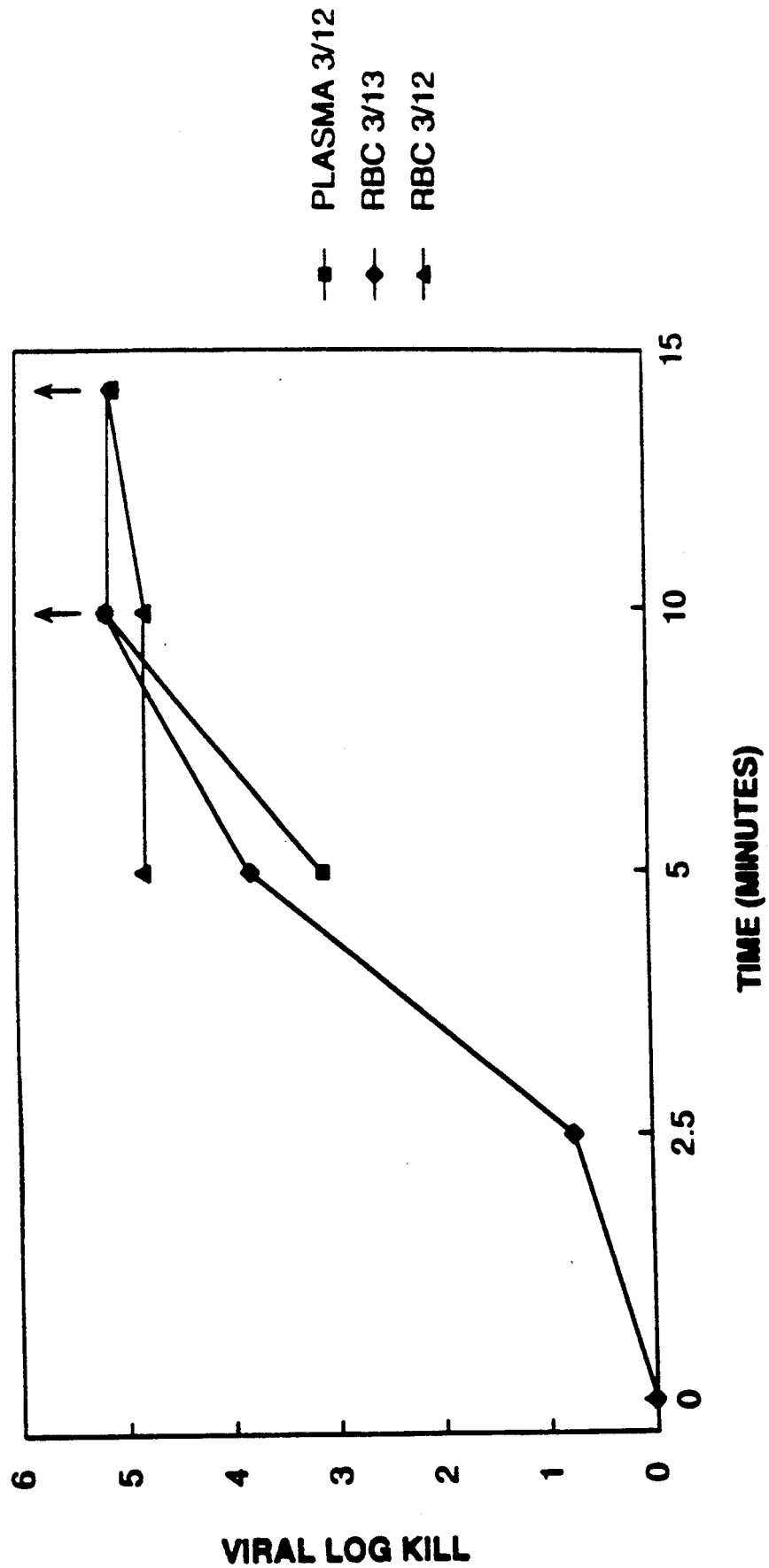

WAVELENGTH-SPECIFIC CYTOTOXIC AGENTS

CROSS-REFERENCE TO RELATED PATENT APPLICATION

This application is a division of U.S. Ser. No. 07/718,393 filed Jun. 20, 1991 and now U.S. Pat. No. 5,171,749; which is a continuation-in-part of U.S. Ser. No. 07/414,201 filed Sep. 28, 1989, now U.S. Pat. No. 5,095,030; which is a continuation-in-part of U.S. Ser. No. 07/221,161 filed Jul. 19, 1988 and now U.S. Pat. No. 4,920,143 which is a continuation-in-part of U.S. Ser. No. 07/041,680 filed Apr. 23, 1987 and now U.S. Pat. No. 4,883,790 which is a continuation-in-part of U.S. Ser. No. 07/005,204 filed Jan. 20, 1987 and now abandoned.

FIELD OF THE INVENTION

The invention relates to the use of light absorbing compounds to mediate the destruction of unwanted cells or tissues or other undesirable materials by irradiation or to detect their presence through fluorescence. Specifically, the invention relates to the use of hydromonobenzoporphyrin derivatives having absorption maxima in the range 670–780 nanometers to mediate the irradiation of materials to be destroyed, and to the use of these compounds conjugated to target-specific ligands, such receptor-specific ligands, or immunoglobulins or their immunospecific fragments, to focus the effects of the irradiation on particular targets.

BACKGROUND OF THE INVENTION

The use of hematoporphyrin and its acetylated derivative mixture hematoporphyrin derivative (HPD) systemically, combined with irradiation, for the detection and treatment of malignant cells has, by this time, some considerable history. HPD is a mixture of porphyrins including hematoporphyrin itself, hydroxyethyl vinyl deuteroporphyrin, protoporphyrin, and dihematoporphyrin ethers. (See, e.g., "Porphyrin Photosensitization," Kessel, D., et al., eds. (1983) Plenum Press.)

HPD seems "naturally" capable of localizing in malignant cells. When irradiated, it has two properties which make it useful. First, when irradiated with ultraviolet or visible light, it is capable of fluorescence, and thus is useful in diagnostic methods related to detection of malignancy (see, for example, Kessel, D., et al. (supra); Gregory, H. B., Jr., et al., *Ann Surg* (1968) 167:827–829). Also important is the capacity of HPD, when irradiated with visible light, to exhibit a cytotoxic effect on the cells or other tissue in which it is localized (see, for example, Diamond, I., et al., *Lancet* (1972) 2:1175–1177; Dougherty, T. J., et al., *Cancer Research* (1978) 38:2628–2635; Dougherty, T. J., et al., "The Science of Photo Medicine" (1982) J. D. Regan & J. A. Parrish, eds., pp. 625–638; Dougherty, T. J., et al., "Cancer: Principles and Practice of Oncology" (1982) V. T. DeVita Jr., et al., eds., pp. 1836–1844). Although it has not been definitively established, the effect of HPD in killing cells seems to be due to the formation of singlet oxygen upon irradiation (Weishaupt, K. R., et al., *Cancer Research* (1976) 36:2326–2329). Several mechanisms for this effect have been proposed, and it has been shown that the active ingredient(s) in HPD which mediates the cytotoxic effect of visible light irradiation is the mixture of dihematoporphyrin ethers (DHE) (Dougherty, T. J., et al., "Porphyrin Localization and Treatment of Tumors" (1984) pp. 301–314; Dougherty, T. J., *CRC Critical Reviews in Oncology/Hematology* (1984) Z:83–116).

A purified form of the active component(s) of HPD is obtained by adjustment of pH to cause aggregation and recovery of the aggregate, as disclosed in U.S. Pat. Nos. 4,649,151, 4,866,168, 4,889,129 and 4,932,934. The purified form called DHE in the patent, is marketed under the trademark Photofrill® II and has been used in a manner completely analogous to HPD.

In addition to in vivo therapeutic and diagnostic protocols for tumors as described in the above-cited patent, the porphyrins, including HPD and its more purified derivatives, can be used in other in vivo and in vitro applications. For example, photosensitizers are useful in the detection and treatment of atherosclerotic plaques as described in U.S. Pat. Nos. 4,512,762 and 4,577,636. U.S. Pat. Nos. 4,500,507 and 4,485,806 describe the use of radiolabeled porphyrin compounds, including HPD, for tumor imaging. U.S. Pat. No. 4,753,958 to the University of California describes the use of topical application of porphyrin sensitizers for diagnosis and treatment of skin diseases. U.S. Pat. Nos. 4,748,120 and 4,878,891 describe the use of photosensitizers in the treatment of whole blood or blood components. Photochemical decontamination treatment of blood and components is also described in U.S. Pat. No. 4,727,027 where the photosensitizer is furocoumarin and its derivatives. In addition, viruses are inactivated in therapeutic protein compositions in vitro as disclosed in U.S. Pat. No. 4,268,947.

The successful treatment of AIDS-related oral Kaposi's Sarcoma with the related photosensitizer Photofrin® II porfimer sodium was described by Schweitzer, V. G., at al., *Otolaryncrology—Head and Neck Surgery* (1990) 102:639–649. It is expected that the modified porphyrins of the present invention will also be effective in regard to this indication and that the sole related side effect—hypersensitivity to sunlight—will be avoided due to the lower dose levels required for the invention compounds.

While the treatment of tumors and other undesirable targets with HPD relies on the intrinsic ability of HPD to localize in malignant or other relevant cells or targets, a considerable improvement and refinement in specificity has been achieved by conjugating the hematoporphyrin to target-specific antibodies. For example, when hematoporphyrin was coupled to monoclonal antibodies directed to a murine myosarcoma cell line Ml, administration of anti-Ml hematoporphyrin-conjugates to tumor-bearing animals followed by exposure to incandescent light resulted in the suppression of MI growth (Mew, D., et al., *J. Immunol* (1983) 130:1473–1477). In additional work, hematorphyrin was conjugated to a monoclonal antibody specific to an antigen associated with a human leukemia (CAMAL) and the conjugates were shown to mediate the irradiation-induced killing of leukemic cells specifically, in vitro (Mew, D., et al., *Cancer Research* (1985) 45:4380–4386). Conjugation of the related compound chlorin $e_6$ to anti-T cell Mab has also been reported (Oseroff, A. R., et al., *Proc Natl Acad Sci USA* (1986) 83:8744–8748).

While the conjugation of hematoporphyrin to immunoglobulins specific for targeted cells refines the ability of the hematoporphyrin to home to the desired cells or tissue, this still does not solve another problem ancillary to this general therapeutic approach, namely that the wavelength for irradiation required to activate the hematoporphyrin or HPD, which is in the range of 630 nanometers, is also an energy which is readily absorbed by the endogenous porphyrins and other natural chromophores in the blood and other tissues. Therefore, relatively large amounts of the hematoporphyrin or HPD must be administered, often resulting in oversensitization of the patient to light in general. It would be desirable to administer compounds to mediate the effects of irradiation in a lower amount and with higher clearance rates, thus avoiding the problems of hypersensitivity exhibited nonspecifically throughout the subject organism. The activity of certain of these compounds was described in a paper by Richter, A. M., et al., in *J Natl Cancer Inst* (1987) 79:1327-1332, mailed to subscribers on 19 January 1988. The invention is directed to the use of such compounds.

DISCLOSURE OF THE INVENTION

The invention provides light absorbing compounds capable of exhibiting light-mediated cytotoxic and diagnostic effects. In addition to their in vitro use, these compounds may be administered in in vivo relatively low dosage due to their capability to absorb radiation whose energy range is outside of that normally strongly absorbed by the components present in high concentration in the blood or other tissues, in particular, the porphyrin residues normally associated with hemoglobin and myoglobin. Therefore, by providing these modified porphyrins for in vivo treatment at lower concentration, hypersensitivity of nontarget tissues is reduced, and the irradiation treatment can be conducted at a wavelength at which the native chromophores do not compete as effectively for photons with the active compounds, resulting in greater depth of penetration of the light. Similar advantages accrue in in vitro treatment of colored materials, such as blood samples.

These photoactive compounds are modified porphyrins which, by virtue of their derivatization, undergo a shift in absorption maxima so that they appear green rather than red, indicating their absorption of wavelengths in the red-orange range. This collection of derivatives has therefore been nicknamed "green porphyrin" (Gp) and has been shown to confer sensitivity on target cells at concentrations greater than 10-fold lower than those required for hematoporphyrin (Hp) or HPD.

The Gp is selected from a group of porphyrin derivatives obtained using Diels-Alder reactions of acetylene derivatives with protoporphyrin under conditions which effect a reaction at only one of the two available conjugated, nonaromatic diene structure present in the protoporphyrin-IX ring system (rings A and B). The formulas shown in FIG. 1 represent the green porphyrins of the invention. These compounds are shown in the figure with hydrogen occupying the internal ring nitrogens; however, it is understood that the metalated forms wherein a cation replaces one or both of these hydrogens can also be employed. It is also understood that these compounds can be labeled either by replacement of one or more of the atoms in the structure by its radioactive form, or by coupling to a radioisotope such as a radioactive metal or, for example, a radioisotope of iodine.

For convenience, an abbreviation of the term hydro-monobenzoporphyrin derivative—"BPD"—is generally used to refer to compounds of formulas 3 and 4 of FIG. 1, as these are the preferred forms of Gp.

Furthermore, dimeric forms of the Gp can be provided, thus amplifying the ability of the Gp compound to absorb light on a per mole basis. Dimeric and multimeric forms of Gp/porphyrin combinations can also be employed, providing additional absorption wavelengths.

The modified porphyrins (referred to as "green porphyrin" or "Gp" herein) of the invention can be conjugated to specific ligands reactive with a target, such as receptor-specific ligands or immunoglobulins or immunospecific portions of immunoglobulins, permitting them to be more concentrated in a desired target tissue or substances. This conjugation permits further lowering of the required dose levels since the material is not wasted in distribution into other tissues whose destruction, far from being desired, must be avoided.

Thus, in one aspect, the invention relates to methods of locating target methods or effecting cytotoxicity by photosensitizing the target materials using the hydro-monobenzoporphyrins of the invention either alone or as conjugates. The hydro-monobenzoporphyrins are green porphyrins (Gp) as shown in FIG. 1 or their metalated or labeled forms, and are localized specifically in vivo to certain target tissues, where their presence can be detected by fluorescence upon excitation using absorbed wavelengths, or by other means when the Gp is provided with additional or alternate labeling. As indicated above, the specificity of the Gp can be further enhanced by conjugation to ligands specific for the target. In addition, when the Gp is irradiated in situ using light in the visible absorption range, photoactivation results in cytotoxicity to the surrounding tissue. While the absorption spect. .n also includes shorter wavelengths, there is an especially useful absorption maximum in the 670-780 nm range. Cells to which the Gp is normally attracted include tumor cells, and neoplastic cells in general, as well as bacteria, virus, atherosclerotic plaque, restenotic tissue, lesions and other diseased tissues. The method can be applied either in vivo or in vivo, and, when applied in vivo, can be localized, including topical, or systemic, including oral, administration.

In another aspect, the invention relates to certain specific Gp compounds including those of formulas 3 and 4 designated herein "BPD," that are partially hydrolyzed forms containing free (non-esterified) carboxylic acid moieties or their salts in the $R^3$ substituents. The invention also relates to labeled forms of these compounds.

In other aspects, the invention relates to conjugates of the formulas Re*-L-Gp and Ig-L-Gp wherein Re* represents a ligand which is specific to, and capable of, binding a receptor at a cell surface, Ig represents an immunoglobulin or an immunologically reactive portion thereof, Gp represents a hydro-monobenzoporphyrin having an absorption maximum in the range of 670-780 nanometers, and L represents either a covalent bond linking these components or a linking moiety covalently linked to each of the Re* or Ig and Gp.

The invention is also directed to tripartite complexes which include Re*-L-Gp or Ig-L-Gp further conjugated to or associated with a label. The label may be bound either to the targeting component or to the Gp or both.

In another aspect, the invention relates to pharmaceutical compositions containing these active ingredients.

MODE OF CARRYING OUT THE INVENTION

The Hydro-monobenzoporphyrins (Gp)

Figure 1:
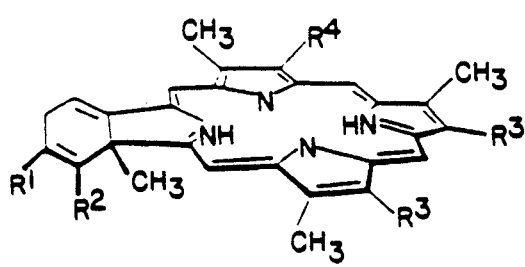
FIG. 1 shows the structure of green porphyrin (Gp) compounds used in the methods and conjugates of the invention.

All of the compositions of the invention employ as the light absorbing compound, a derivative of the protoporphyrin ring system which has a light absorption maximum in the range of 670-780 nanometers. FIG. 3 shows the absorption spectrum of one of the compounds of the invention shown in FIG. 2, BPD-DA, wherein $R^1$ and $R^2$ are carbomethoxy, in comparison to HPD and Photofrin® II compositions. Only BPD-DA has a major absorption peak at about 685 nm.

In general, this shift is achieved by effectively saturating one of the two $\pi$-bonds in one, but not two, of the four pyrrole rings which constitute the typical porphyrin system. In protoporphyrin-IX two of the pyrroles contain vinyl substitutions such that the exocyclic $\pi$-bond is conjugated to one of the two $\pi$-bonds in the ring. A Diels-Alder reaction involving one of these conjugated systems with an acetylene derivative dienophile results in a fused cyclohexadiene—referred to herein as "hydrobenzo"—fused to the A or B ring, as shown in formulas 1 and 2. Rearrangement of the $\pi$ system in the hexadiene ring results in the compounds of formulas 3 and 4; reduction provides the compounds of formulas 5 and 6. All of these compounds provide the desired bathochromic shift in absorption maximum.

Specific preparation of some compounds useful in the invention or their precursors is described by Morgan, A. R., et al., *J Chem Soc Chem Commun* (1984) pp. 1047-1048; and by Pangka, B. S., et al., *J Organic Chem* (1986) 51:1094. As described in these publications, it had earlier been reported that protoporphyrin-IX dimethyl ester, when reacted with strong Diels-Alder dienophile reagents such as tetracyanoethylene, is derivatized to the hydro-dibenzo derivatives. However, it is clear that, as shown by these references, when acetylene is derivatized with more weakly electron withdrawing groups and used as a Diels-Alder reagent, hydro-monobenzo derivatives are formed. Thus, there are obtained directly from reaction of protoporphyrin with, for example dimethyl acetylene dicarboxylate (DMAD), compounds shown as formulas 1 and 2 of FIG. 1, wherein $R^1$ and $R^2$ represent the substituents on the original acetylene-derived Diels-Alder reagent, $R^1C \equiv CR^2$— in this case, carbomethoxy. $R^1$ and $R^2$ are, generally, specifically carbalkoxy groups such as carbomethoxy or carboethoxy. $R^3$ represents substituents present on the porphyrin used in the reaction or substituents derived therefrom. In the Morgan reference, the reaction substrate was protoporphyrin-IX dimethyl ester; thus the ligand $R^3$ was, in all cases, 2-carbomethoxyethyl or 2-carboethoxyethyl.

The disclosed substituents in the Morgan and Pangka references for the acetylene-derived dienophile include phenylsulfonyl—i.e., $SO_2$ Ph, either as a single substituent, as described in the foregoing references (b-phenylsulfonylpropiate) or, putatively, wherein both $R^1$ and $R^2$ are sulfonyl derivatives. In general, $R^1$ and $R^2$ are each, independently, moderate electron-withdrawing substituents, and are, most commonly, carbalkoxy, or alkyl or aryl sulfonyl, or any other activating substituents, which are not sufficiently electron-withdrawing to result in reaction with both A and B rings rather than reaction with only one, such as cyano or —CONR-$^5$CO— wherein $R^5$ is aryl or alkyl. One of $R^1$ and $R^2$ may optionally be H while the other is an electron withdrawing substituent of sufficient strength to facilitate the Diels-Alder reaction.

As used herein, carboxy is, as conventionally defined, —COOH and carbalkoxy is —COOR, wherein R is alkyl; carboxyalkyl refers to the substituent —R'—COOH wherein R' is alkylene; carbalkoxyalkyl refers to —R'—COOR wherein R' and R are alkylene and alkyl respectively. Alkyl is a saturated straight or branched chain hydrocarbyl of 1-6 carbon atoms such as methyl, n-hexyl, 2-methylpentyl, t-butyl, n-propyl, and so forth. Alkylene is as alkyl except that the group is divalent. Aryl or alkyl sulfonyl moieties have the formula $SO_2R$ wherein R is alkyl as above-defined, or is aryl, wherein aryl is phenyl optionally substituted with 1-3 substituents independently selected from halo (fluoro, chloro, bromo or iodo), lower alkyl (1-4C) or lower alkoxy (1-4C). In addition, one or both $R^1$ of $R^2$ can itself be aryl—i.e., phenyl optionally substituted as above defined.

As shown in FIG. 1, the adduct formed by the reaction of $R^1$—C≡C—$R^2$ with the protoporphyrin-IX ring system ($R^3$ is a protected form of 2-carboxyethyl such as 2-carbomethoxyethyl or 2-carboethoxyethyl; $R^4$ is $CH=CH_2$) are compounds of the formulas 1 and 2 wherein the compound in formula 1 results from addition to the A ring and formula 2 results from addition to the B ring. In these resulting products of formulas 1 and 2, $R^4$ remains $CH=CH_2$, however this vinyl group is readily derivatized to other embodiments of $R^4$ by addition to or oxidation of the vinyl ring substituent of ring B in formula 1 or ring A in formula 2. The addition or oxidation products can be further substituted if the added substituents are functional leaving groups—for example —Br may be substituted by —OH, —OR (R is alkyl 1-6C as above), or —NH$_2$, —NHR, —NR$_2$, etc. In preferred embodiments, one of the added substituents is hydrogen, and the other is selected from the group consisting of halo (fluoro, chloro, bromo or iodo), hydroxy, lower alkoxy, amino or an amide, sulfhydryl or an organo-sulfide or can be, itself, hydrogen. Addition to the vinyl group does not appreciably change the absorption spectrum of the resulting compound. The product of the Markonikov addition of water provides a substituent structure analogous to the hematoporphyrin ring system at the relevant ring. Thus, the compounds of the invention include various groups as $R^4$, including substituents which provide additional porphyrin or porphyrin-related ring systems, as will be further described below.

$R^3$ in protoporphyrin-IX is 2-carboxyethyl ($-CH_2CH_2COOH$). However, the nature of $R^3$ (unless it contains a $\pi$-bond conjugated to ring $\pi$-bond), is ordinarily not relevant to the progress of the Diels-Alder reaction or to the effectiveness and absorption spectrum of the resulting product. $R^3$ can thus be, for example, lower alkyl (1–4 C), or 1-carboxyalkyl (2–6C) or the esters or amides thereof. The $R^3$ substituent may also be substituted with halogen as above-defined, or with other nonreactive substituents. However, as the convenient starting materials for the Gp compounds of the invention are the naturally occurring porphyrins, the preferred substituents for $R^3$ are $CH_2CH_2COOH$ or $-CH_2CHR_2COOR$, wherein R is alkyl (1–6C).

It should be noted that while the nature of the $R^3$ substituent does not ordinarily influence the course of the Diels-Alder reaction by altering the nature of the diene substrate, derivatization may be necessary to promote the reaction by providing suitable solubility characteristics or to prevent interference with the reaction. Thus, the Diels-Alder reactions described by Morgan et al. and by Pangka et al. utilized the dimethylester of protoporphyrin-IX as a substrate in order to prevent interference with the reaction by the free carboxyl group and to provide suitable solubility characteristics.

In the BPD compounds of the invention, it has been found advantageous to hydrolyze or partially hydrolyze the esterified carboxy group in $-CH_2CH_2COOR$. The hydrolysis occurs at a much faster rate than that of the ester groups of $R^1$, $R^2$, and the solubility and biodistribution characteristics of the resulting compounds are more desirable than those of the unhydrolyzed form. Hydrolysis results in the diacid or monoacid products (or their salts).

The hydro-monobenzoporphyrins which directly result from the Diels-Alder reaction described in the cited references can also be isomerized as therein described (see Morgan et al. and Pangka et al., supra) to compounds of formulas shown as 3 and 4 of FIG. 1 by treatment with suitable reagents such as triethylamine (TEA) in methylene chloride or 1,5-diaza bicyclo 8 5.4.01] undec-5-ene (DBU). The stereochemistry of the product is determined by the choice of reagent.

The depictions of compounds 3 and 4 in FIG. 1 do not show the relative position of the exocyclic methyl group (ring A of formula 3 and ring B of formula 4) with respect to the $R^2$ substituent. It has been found by these authors that rearrangement using TEA gives cis geometry for the angular methyl group and $R^2$, while treatment with DBU results in the trans product. This cis product is evidently kinetically controlled since treatment of the cis product with DBU results in a further rearrangement to trans stereochemistry. Thus, formulas 3 and 4 of FIG. 1 show the rearranged products generically, from either TEA or DBU catalyzed rearrangement in rings A and B respectively.

In addition, the Diels-Alder products can be selectively reduced by treating with hydrogen in the presence of palladium on charcoal to give the saturated ring analogs, shown as formulas 5 and 6 in FIG. 1, corresponding to the respective Diels-Alder products of rings A and B. These reduced products are less preferred embodiments, and are less useful in the method of the invention than the compounds of formulas 1–4.

The description set forth above with respect to the compounds of formulas 1 and 2 concerning derivatization by conversion of the remaining vinyl substituent ($R^4$) and with respect to variability of $-R^3$ applies as well to the compounds of formulas 3, 4, 5 and 6.

The compounds of formulas 3 and 4 (BPD), and especially those which have hydrolyzed and partially hydrolyzed carbalkoxy groups in $R^3$, are most preferred. compounds of the invention which contain $-COOH$ may be prepared as the free acid or in the form of salts with organic or inorganic bases.

It will be noted that many of the compounds of FIG. 1 contain at least one chiral center and therefore exist as optical isomers. The conjugates and methods of the invention include compounds having both configurations of the chiral carbons, whether the compounds are supplied as isolates of a single stereoisomer or are mixtures of enantiomers and/or diastereomers. Separation of mixtures of diastereomers may be effected by any conventional means; mixtures of enantiomers may be separated by usual techniques of reacting them with optically active preparations and separating the resulting diastereomers.

It should further be noted that the reaction products may be unseparated mixtures of A and B ring additions, e.g., mixtures of formulas 1 and 2 or 3 and 4 or 5 and 6. Either the separated forms—i.e., formula 3 alone or 4 alone, or mixtures in any ratio may be employed in the methods of therapy and diagnosis set forth herein.

The name "dihydro"-monobenzoporphyrin describes the direct and rearrangement products of the Diels-Alder reaction of the porphyrin ring system with $R^1C=C-R^2$; "tetrahydro"-monobenzoporphyrin describes the foregoing reduced products of formulas 5 and 6, and "hexahydro"-monobenzoporphyrin describes the analogs containing the exocyclic "benzo" ring completely reduced. Hydromonobenzoporphyrin is used generically to include all three classes of oxidation state. The monobenzoporphyrins per se are outside the scope of the invention as their absorption maxima do not fall within the required range.

Figures 1, 2:
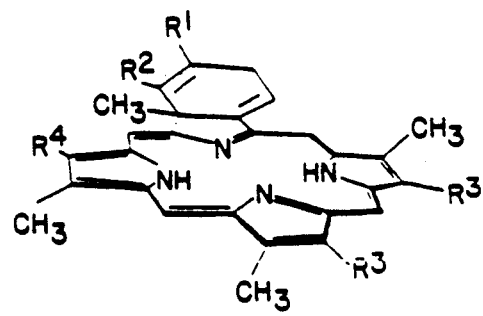
FIG. 2 shows the structure of four preferred forms of the hydro-monobenzoporphyrin derivative of formulas 3 and 4 (BPDs).
Figures 1, 2, 3:
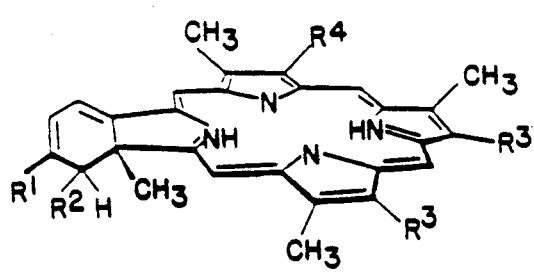
FIG. 3 shows a comparative absorption spectrum of a BPD compound and prior art compositions.

FIG. 2 shows four particularly preferred compounds of the invention which have not been previously described in the art. These compounds are collectively designated benzoporphyrin derivative (BPD) as they are forms of Gp having the formula 3 or 4. These are hydrolyzed or partially hydrolyzed forms of the rearranged products of formula 3 and 4, wherein one or both of the protected carboxyl groups of $R^3$ are hydrolyzed. The ester groups at $R^1$ and $R^2$ hydrolyze relatively so slowly that conversion to the forms shown in FIG. 2 is easily effected.

For purposes of this description, $R^3$ is $-CH_2CH_2COOR^{3'}$. As shown in FIG. 2, each $R^{3'}$ is H in preferred compound BPD-DA, $R^1$ and $R^2$ are carbalkoxy, and derivatization is at ring A; BPD-DB is the corresponding compound wherein derivatization is at ring B. BPD-MA represents the partially hydrolyzed form of BPD-DA, and BPD-MB, the partially hydrolyzed form of BPD-DB. Thus, in these latter compounds, $R^1$ and $R^2$ are carbalkoxy, one $R^{3'}$ is H and the other $R^{3'}$ is alkyl (1–6C). The compounds of formulas BPD-MA and BPD-MB may be homogeneous wherein only the C ring carbalkoxyethyl or only the D ring carbalkoxyethyl is hydrolyzed, or may be mixtures of the C and D ring substituent hydrolyzates. In addition, mixtures of any two or more of BPD-MA, -MB, -DA and -DB may be employed in the method of the invention.

As these hydrolyzed forms of the Diels-Alder product are previously undisclosed, the invention is also directed to these compounds. Thus, in another aspect, the invention is directed to compounds of the formulas shown in FIG. 2 wherein $R^1$ and $R^2$ are as above defined, and R is alkyl (1-6C). Preferred are embodiments wherein $R^1$ and $R^2$ are carbalkoxy, especially carbomethoxy or carboethoxy.

Certain other embodiments wherein $R^4$ is other than vinyl or wherein $R^3$ is a nonnative substituent are also not disclosed in the art and the invention is directed to them, i.e., the invention is directed to the compounds shown in FIG. 1 wherein each $R^1$ and $R^2$ is independently selected from the group consisting of carbalkoxy (2-6C), alkyl (1-6C) sulfonyl, aryl (6-10C) sulfonyl, aryl (6-10C); cyano; and —$CONR^5CO$— wherein $R^5$ is aryl (6-10C) or alkyl (1-6C);

each $R^3$ is independently carboxyalkyl (2-6C) or a salt, amide, ester or acylhydrazone thereof, or is alkyl (1-6C); and $R^4$ is $CHCH_2$, $CHOR^{4'}$, —CHO, —$COOR^{4'}$, $CH(OR^{4'})CH_3$, $CH(OR^{4'})CH_2OR^{4'}$, —$CH(SR^{4'})CH_3$, —$CH(NR^{4'}{}_2)CH_3$, —$CH(CN)CH_3$, —$CH(COOR^{4'})CH_3$, —$CH((OOCR^{4'})CH_3$, —$CH(halo)CH_3$, or —$CH(halo)CH_2(halo)$, wherein $R^{4'}$ is H, alkyl (1-6C) optionally substituted with a hydrophilic substituent, or wherein $R^4$ is an organic group of <12C resulting from direct or indirect derivatization of vinyl, or wherein $R^4$ is a group containing 1-3 tetrapyrrole-type nucleic of the formula —L—P as herein defined;

wherein when $R^4$ is $CHCH_2$, both $R^3$ cannot be 2-carbalkoxyethyl.

Compounds of the formulas 3 and 4 and mixtures thereof are particularly preferred. Also preferred are those wherein $R^1$ and $R^2$ are the same and are carbalkoxy, especially carboethoxy; also preferred are those wherein $R^4$ is —$CHCH_2$, $CH(OH)CH_3$ or —$CH(halo)CH_3$, or is a group containing 1-3 tetrapyrrole-type nuclei of the formula —L—P (defined below).

As used herein, "tetrapyrrole-type nucleus" represents a four-ring system of the skeleton:

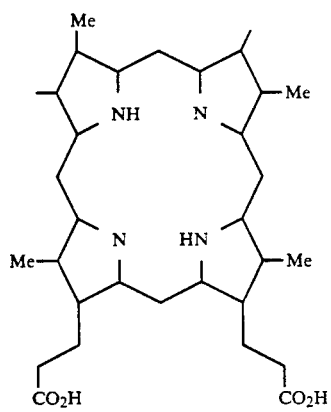

which is abbreviated

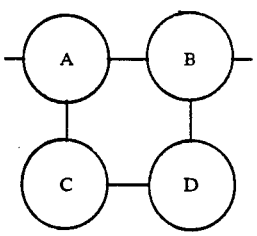

and a salt, ester, amide or acylhydrazone thereof, which is highly conjugated. It includes the porphyrin system, which is, in effect, a completely conjugated system, the chlorin system, which is, in effect, a dihydro form of the porphyrin, and the reduced chlorin system, which is a tetrahydro form of the completely conjugated system. When "porphyrin" is specified, the completely conjugated system is indicated; Gp is effectively a dihydro form of the porphyrin system.

One group of compounds of the invention is that wherein the substituent $R^4$ includes at least one additional tetrapyrrole-type nucleus. The resulting compounds of the invention are dimers or oligomers in which at least one of the tetrapyrrole-type ring systems is Gp. Linkage between the Gp moiety through the position of $R^4$ to an additional tetrapyrrole-type ring system may be through an ether, amine or vinyl linkage. Additional derivatization in the case of porphyrin ring systems which have two available substituent positions (in both A and B rings) corresponding to $R^4$ can also be formed, as further described below.

As stated above, the compounds of formulas shown in FIG. 1 include those wherein the embodiment of $R^4$ is formed by addition to the vinyl groups of initial Gp products. Thus, $R^4$ can be any substituent consistent with that formed by a facile addition reaction. Thus, both added substituents can be, for example, OH or halo, and these substituents can be further substituted, or the addition reagent may be of the form HX wherein H is added to the ring-adjacent carbon to provide $R^4$ of the form

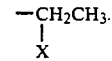

The vinyl group can also be oxidized to obtain $R^4$ as $CH_2OH$, —CHO, or COOH and its salts and esters.

Thus, in general $R^4$ represents any substituents to which the vinyl group —$CH=CH_2$ is readily converted by cleavage or addition, and further resultants of reaction of leaving groups with additional moieties. Typical $R^4$ substituents include:

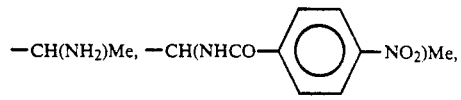

-continued

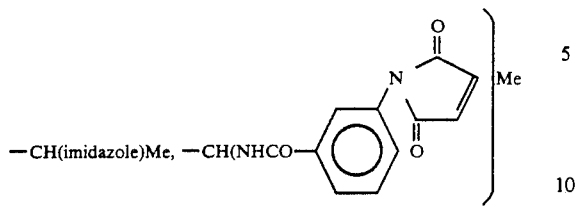

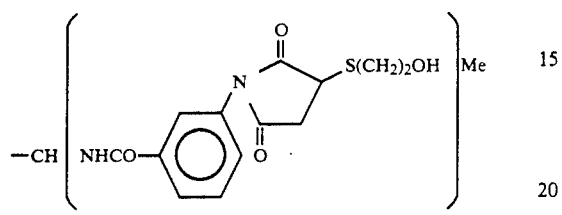

CH(OH)Me, —CHBrMe, —CH(OMe)Me, —CH-(pyridinum bromide)Me, —CH(SH)Me and the disulfide thereof, —CHOHCH$_2$OH, —CHO, and —COOH or —COOME.

When R is —L—P, the substituent formula "—L—P" represents a substituent wherein —L— is selected the group consisting of

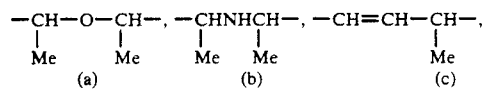

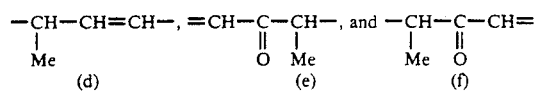

and P is selected from the group consisting of Gp wherein Gp is of the formula 1-6 shown in FIG. 1, but lacking $R^4$ and conjugated through the position shown in FIG. 1 as occupied by $R^4$ to L, and a porphyrin of the formula

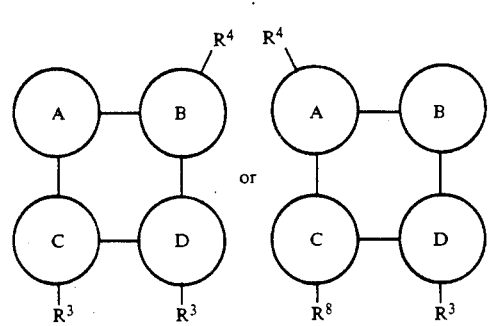

wherein $R^3$ and $R^4$ are as above-defined, and the unoccupied bond is then conjugated to L. It is understood that the abbreviation represents a porphyrin of the formula:

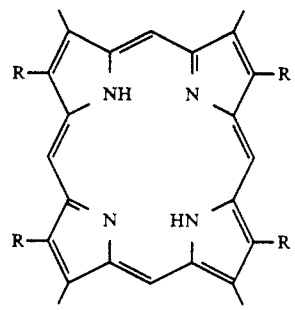

wherein each R is independently H or lower alkyl (1-4C).

(It is also understood that when —L— is of the formula (e) or (f), the ring system to which the double bond is attached will have a resonance system corresponding to

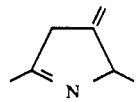

in the ring to which the double bond is attached, as shown.)

Typical embodiments of —L—P include

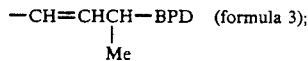

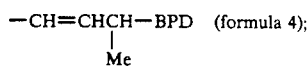

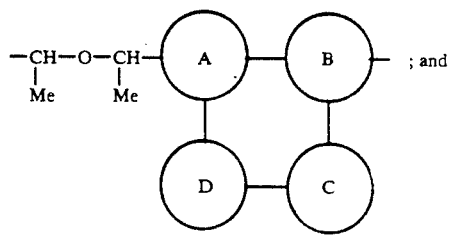

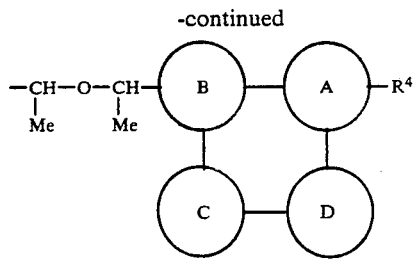

wherein $R^4$ is as above defined. Thus, compounds of the invention include:

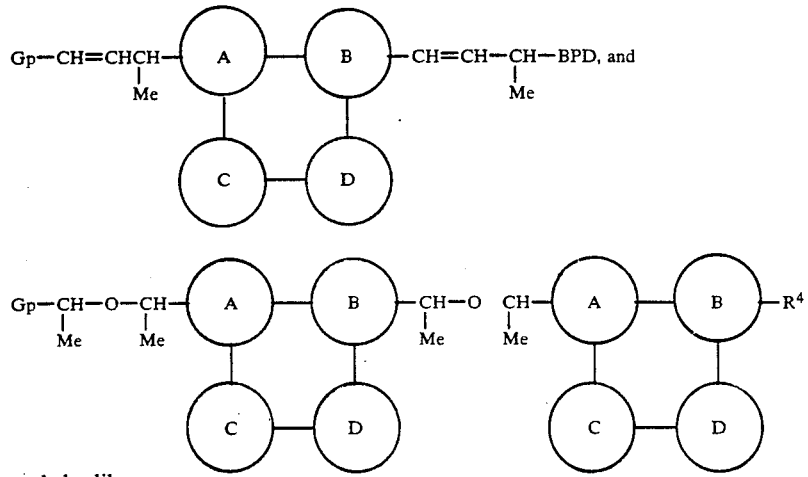

and the like.

Preparation of the Dimers and oligomers

The dimers and oligomeric compounds of the invention can be prepared using reactions analogous to those for dimerization and oligomerization of porphyrins per se. The green porphyrins or green porphyrin/porphyrin linkages can be made directly, or porphyrins may be conjugated, flowed by a Diels-Alder reaction of either or both terminal porphyrins to convert to the corresponding green porphyrin.

For formation of compounds of the invention where —L— is of the formula

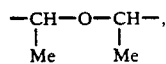

i.e., an ether linkage, the Gp vinyl group is converted to the halide, preferably the chloride, by treating the Gp or porphyrin in a solution of, for example, methylene chloride with HBr to recover the addition product. The resulting product is harvested by evaporation in vacuo, redissolved in methylene chloride and added to an insoluble base such as solid potassium carbonate. To this is added an equivalent of the tetrapyrrole-type nucleus "P" to be linked wherein the reactive $R^4$ moiety of "P" is 1-hydroxyethyl. The mixture is stirred for the appropriate amount of time, around 12 hours, generally, and the resulting diastereomeric pair of dimers (the enantiomeric paired form and a meso form) can be separated from the mixture chromatographically. The tetrapyrrole-type nucleus represented by "P" in this procedure can be either another Gp or a porphyrin.

If the "P" substituent is a porphyrin, an additional vinyl group may be made available for further halogenation and further reaction to form higher order oligomers.

For embodiments wherein —L— contains a vinyl group, the dimers are obtained by treating Gp or porphyrin wherein $R^4$ is 1-hydroxyethyl with an equivalent amount of the linking tetrapyrrole-type nucleus also having the linking $R^4$ as 1-hydroxyethyl with a strong, nonnucleophilic acid, such as trifluoromethyl sulfonic acid. This treatment results in precipitation of the resulting methylpropenyl linked dimer. (The ether-linked dimer can be formed as a side product in this reaction by substituting alternative acids such as sulfuric acid.)

The amino-linked compounds can be formed by treatment of the vinyl group with HBr followed by treatment with the appropriate amine to obtain the desired linkage.

The Target-Specific Component

The target-specific component can be, for example, an immunoglobulin or portion thereof or a ligand specific for receptor.

The immunoglobulin component can be any of a variety of materials. It may be derived from polyclonal or monoclonal antibody preparations and may contain whole antibodies or immunologically reactive fragments of these antibodies such as F(ab')$_2$, Fab, or Fab' fragments. Use of such immunologically reactive fragments as substitutes for whole antibodies is well known in the art. See, for example Spiegelberg, H. L., in "Immunoassays in the Clinical Laboratory" (1978) 3:1-23.

Polyclonal anti-sera are prepared in conventional ways by injecting a suitable mammal with antigen to which antibody is desired, assaying the antibody level in serum against the antigen, and preparing anti-sera when the titers are high. Monoclonal antibody preparations may also be prepared conventionally such as by the method of Koehler and Milstein using peripheral blood lymphocytes or spleen cells from immunized animals and immortalizing these cells either by viral infection, by fusion with myelomas, or by other conventional procedures, and screening for production of the desired antibodies by isolated colonies. Formation of the fragments from either monoclonal or polyclonal preparations is effected by conventional means as described by Spiegelberg, H. L., surra.

Particularly useful antibodies exemplified herein include the monoclonal antibody preparation CAMAL-1 which can be prepared as described by Malcolm, A., et al., *Ex Hematol* (1984) 12:539-547; polyclonal or monoclonal preparations of anti-M1 antibody as described by Mew, D., et al., *J Immunol* (1983) 130:1473-1477 (supra); and B16G antibody which is prepared as described by Maier, T., et al., *J Immunol* (1983) 131:1843; Steele, J. K., et al., *Cell Immucol* (1984) 90:303.

The foregoing list is exemplary and certainly not limiting; once the target tissue is known, antibody specific for this tissue may be prepared by conventional means. Therefore the invention is applicable to effecting toxicity against any desired target.

The ligand specific for receptor, Re*, refers to a moiety which binds a receptor at cell surfaces, and thus contains contours and charge patterns which are complementary to those of the receptor. The ligand specific for receptor is symbolized in the formulas of the compounds of the invention as Re*, wherein the asterisk indicates that the moiety bound in the compound of the invention is not the receptor itself, but a substance complementary to it. It is well understood that a wide variety of cell types have specific receptors designed to bind hormones, growth factors, or neurotransmitters. However, while these embodiments of ligands specific for receptor are know and understood, the phrase "ligand specific for receptor," as used herein, refers to any substance, natural or synthetic, which binds specifically to a receptor.

Examples of such ligands include the steroid hormones, such as progesterone, estrogens, androgens, and the adrenal cortical hormones; growth factors, such as epidermal growth factor, nerve growth factor, fibroblast growth factor, and so forth; other protein hormones, such as human growth hormone, parathyroid hormone, and so forth; and neurotransmitters, such as acetylcholine, serotonin, and dopamine. Any analog of these substances, such as agonists or antagonists, which succeeds in binding to the receptor is also included.

Linkage

The conjugation of the target-cell-specific component to the hydro-monobenzoporphyrin can be effected by any convenient means. For proteins, such as Ig and certain Re*, a direct covalent bond between these moieties may be effected, for example, using a dehydrating agent such as a carbodiimide, in which case L represents a covalent bond. A particularly preferred method of covalently binding hydro-monobenzoporphyrins to the immunoglobulin moiety is treatment with 1-ethyl-3-(3-dimethylamino propyl) carbodiimide (EDCI) in the presence of a reaction medium consisting essentially of dimethyl sulfoxide (DMSO). A preparation using this preferred procedure is illustrated in Example 3 below.

Of course, other dehydrating agents such as dicyclohexylcarbodiimide or diethylcarbodiimide could also be used as well as conventional aqueous and partially aqueous media.

Nonprotein receptor ligands can be conjugated to the Gp according to their relevant functional groups by means known in the art.

The active moieties of the conjugate may also be conjugated, through linker compounds which are bifunctional, and are capable of covalently binding each of the two active components. A large variety of these linkers is commercially available, and a typical list would include those found, for example, in the catalog of the Pierce Chemical Co. These linkers are either homo or heterobifunctional moieties and include functionalities capable of forming disulfides, amides, hydrazones, and a wide variety of other linkages.

Other linkers include polymers such as polyamines, polyethers, polyamine alcohols, derivatized to the components by means of ketones, acids, aldehydes, isocyanates, or a variety of other groups.

The techniques employed in conjugating the active moieties of the conjugate include any standard means and the method for conjugation does not form part of the invention. Therefore, any effective technique known in the art to produce such conjugates falls within the scope of the invention, and the linker moiety is accordingly broadly defined only as being either a covalent bond or any linker moiety available in the art or derivable therefrom using standard techniques.

Label

For use in the method of the invention either the green porphyrin compounds per se or the conjugates may be further derivatized to a compound or ion which labels the drug. A wide variety of labeling moieties can be used, including radioisotopes, chromophores, and fluorescent labels. Radioisotope labeling is preferred, as it can be readily detected in vivo.

The compounds which are Gp alone or are conjugates of Gp with a specific binding substance can be labeled with radioisotopes by coordination of a suitable radioactive cation in the porphyrin system. Useful cations include technetium, gallium, and indium. In the conjugates, either or both the specific binding substances can be linked to or associated with label, or the label can be conjugated or coordinated with the Gp moiety itself.

Metal Ions

The compounds of the invention can be administered or used in in vitro methods as shown above or when complexed to appropriate metal ions. As is generally understood in the art, the tetrapyrrole-type nucleus can be treated with an appropriate ion such as magnesium ion, zinc ion, stannous ion, and the like to obtain the metal complex. As stated above, the metal ion may also be a radiolabel. The nature and desirability of the inclusion of a metal ion in the tetrapyrrole-type nucleus depends on the specific application for which the compound is intended. When the inclusion of a metal ion is desired, the desired metal ion can be inserted using the appropriate metal salts under known conditions. For example, zinc ion can be introduced by treating the compound with zinc acetate in 1:1 methylene chloride:-methanol.

Administration and Use

The improved photosensitizing compounds of the invention are thus useful in general, in the manner known in the art for hematoporphyrin derivative and for DHE. These materials are useful in sensitizing neoplastic cells or other abnormal tissue including infectious agents to destruction by irradiation using, preferably, visible light. Upon photoactivation, the compounds seem to have no direct effect; the energy of photoactivation is believed to be transferred to endogenous oxygen to convert it to singlet oxygen. This singlet oxygen is thought to be responsible for the cytotoxic effect. In addition, the invention compounds photoactivated using appropriate excitation wavelengths fluoresce. This fluorescence can be used to localize the tumor or other target tissue.

In general, the same wavelength range can be used for inducing cytotoxicity as for exciting fluorescence; if fluorescence is to be directly observed, however, it is advantageous to use appreciably shorter wavelengths so that the excitation radiation does not interfere with the observation of the fluorescence. However, if a suitably arranged apparatus is employed, the excitation wavelength can be quite close to the fluorescent wavelength. In addition, although all of the green porphyrin compounds of the invention can be activated by light in the wavelength range of 670–780 nm, shorter wavelengths can also be used, if desired, for convenience. In many cases, the absorption spectra show appreciable absorption down to the low 600 nm range as well as at appreciably shorter wavelengths.

The radiation for mediating cytotoxicity or fluorescence emission can be supplied by standard sources of visible radiation, including incandescent or fluorescent light sources using suitable filters, or can be supplied by photodiodes, such as light-emitting diodes at a narrow wavelength range. In addition, laser light is often convenient for the in situ delivery of light to the localized photosensitizer of the invention. Thus, among the sources that have been used in photodynamic therapy and diagnosis in general are quartz, halogen and arc lamp sources, monochromatic light from a fixed wavelength, gold vapor, tunable argon-pump dye laser or other wavelength-specific lasers, and standard visible light sources in general.

Particularly preferred in the therapeutic and diagnostic practice of the invention are light-emitting diodes (LEDS) which produce sufficient radiation to activate the photosensitizing compounds and are relatively inexpensive, small in size, and do not require special utilities for operation. The relatively broad-band light generated from LEDS, as compared to the single wavelength generated by laser radiation, allows advantage to be taken of the broad wavelength absorption of the invention compounds. BPD-MA, for example, has an absorption peak with substantial extinction coefficients extending from 680 nm to 700 nm. The LEDs also contribute less heat to the irradiated biological tissue than do typical filtered broad-band light sources. LEDs are particularly adaptable in cases where relatively large irradiation areas are required as in treatment, for example, of large superficial lesions of skin cancer.

Most LEDs have emission bands of about 20–40 nm and can operate from the green (500 nm) to the near infrared; the LEDs appropriate for the compounds of the invention generally will emit in the range of 600 nm to 800 nm. Multiple LEDs positioned together can generate radiant flux levels of 40 mw/cm$^2$ to 100 mw/cm$^2$ and have. operating lifetimes of 100,000 hours or more. As these are solid state devices, there are no separate components or moving mechanisms, nor is there requirement for maintenance other than replacement. They use low voltages and typically require no temperature regulation.

Typical lasers used in photodynamic therapy and diagnosis involving the compounds of the invention include metal vapor or dye lasers, such as the argon-pumped dye laser or copper vapor-pumped dye laser or Nd:YAG-pumped dye laser, among others. In use, the laser system generally consists of 2-3 separate lasers arranged serially to achieve the desired output wavelength and optical power. Lasers are less efficient in conversion of electrical to optical energy than LEDs—for the argon laser values in the range of 0.01–0.25% are typical—whereas LEDs have electrical-to-light conversion efficiencies of about 8%. LEDs also have longer lifetimes as compared to the 2,000–3,000 hours available from typical argon lasers.

Any suitable light source can be used for irradiation of the tissue to effect cytotoxicity or excite fluorescence in those tissues in which the invention compounds reside. However, light-emitting diodes are preferred.

It is also feasible to generate the photoactivating light using a system which produces light by virtue of a chemical reaction. In these systems, a chemical transition which liberates energy sufficient to excite visible wavelength emissions from a suitable compound is responsible for the radiation. A chemiluminescent system (CLS) wherein a substituted oxamide reacts with hydrogen peroxide in the presence of a sulfonated rubene to produce an intense yellow-red light lasting 10–20 minutes was reported to be useful as an irradiation source in photodynamic therapy by Phillip, M. J., et al., in "Porphyrin Localization in Treatment of Tumors" (1984), Alan R. Liss, Inc., pp. 563–569; Phillip, M. J., et al., *Oncology* (1989) 41:266–272. The CLS is injected directly into the target tumor after the photosensitizer has homed to the target. This CLS, as well as alternative nontoxic light-generating systems, can be used as irradiation sources in the methods of the invention.

In addition to irradiation for excitation of the invention compounds for therapy, additional forms of irradiation which can independently destroy the tissue irradiated can be used to supplement the effect of the photodynamic therapy per se. The use Of X-irradiation or gamma-irradiation as a direct treatment for tumors has been known for many years, and the combination of X-ray therapy with photodynamic therapy using art-known forms of porphyrins his been well documented, for example by Schwartz, S., et al., *U Minn Med Bull* (1955) 27:1–37. A retrospective of this combination treatment was given by Dr. Schwartz at the Third Biennial Meeting of the Third International Photodynamic Association, Jul. 18, 1990, in Buffalo, N.Y. Thus, the therapeutic methods of the invention can employ a variety of irradiation means for activation of the photosensitizer, alone or in combination with additional radiation designed for direct treatment of tumor, said direct treatment radiation typically including X-rays, microwave radiation, and the use of additional photochemicals as chemiluminescent or fluorescent radiation transfer materials.

In addition to additional irradiation, the photodynamic treatment can be accompanied by adjuvant therapy using approaches such as surgery and chemotherapy. Also, PDT potentiators, such as glucose, which depresses tumor pH and results in greater accumulation of the photosensitizer and thus more effective cytotoxicity, can be used. This is suggested by Thomas and Girotti, *Photochem. Photobiol.* (1989) 49:241–247. Other adjuvant treatments which can be used along with photodynamic therapy include the use of protective agents such as cadmium chloride for topical application, misonidazole (MISO), or ethanidazole for protection against direct cellular phototoxicity of intermediate oxygen concentration, or antiinflammatories such as ibuprofen and ASA as protective agents. Additional inhibitors of PDT which can regulate its effect include noradrenaline, propanalol, hydrazine, and phenoxybenzamine.

Typical of the indications targeted for photodynamic treatment include in vivo treatment for destruction of tumor tissue in solid tumors and for dissolution of plaques in blood vessels (see, e.g., U.S. Pat. No. 4,512,762); prevention of restenosis; and treatment of topical conditions such as acne; athlete's foot; warts; papilloma, including venereal, laryngeal and dermal; unwanted tissue in general, such as hair follicles or fat deposits; port wine stains; hypervascularization, including varicose veins and spider veins; and psoriasis. Other indications include the systemic treatment of tumors and neoplastic tissues, such as malignancies that occur in brain, face, mouth, throat, lung, gastric, rectal, prostate, ovarian, breast, skin (basal, melanoma), bone, blood, hematopoietic, lymph, bronchial, cervical, esophageal or colon tissues and Kaposi's Sarcoma. The invention compounds are also useful for treatment of biological products (such as blood for transfusion) for infectious agents, since the presence of a membrane in such agents promotes the accumulation of the drug.

In particular, the invention compounds are useful for eradicating infectious agents, in vivo or ex vivo, including viral contaminants often found in donated blood or blood products. Such infectious and viral contaminants include, for example, bacterial, fungal or parasitic infection, hepatitis B, hepatitis A or hepatitis C virus, human immunodeficiency virus (HIV), cytomegalovirus (CMV), and Epstein-Barr virus. Vesicular stomatitis virus (VSV), while not usually found in human blood, behaves in a similar manner in response to the photodynamic treatment. In addition, parasites such as Trypanosomes or Plasmodium are susceptible targets. All of the foregoing infectious agents can be eradicated by the methods of the invention both in vivo and ex vivo.

For use in in vivo treatment or diagnosis of atherosclerotic plaques or malignancies or infections treated systemically, the compounds of the invention are injected, typically by intravenous injection, and permitted sufficient time to home to the atherosclerotic plaques, malignancies or infective agents, usually about 30 minutes to 3 hours. The plaques or malignancies are then subjected to irradiation for therapeutic effect to dissolve the plaque or destroy the tumor cells. Typical dosages are in the range of 100 $\mu$g/kg to 10 mg/kg of the drug based on the weight of the subject. Due to the accumulation of the drug in the plaques or tumor cells, treatment is effected. As infectious agents are distributed, focus of the radiation on the target can be effected only using whole body radiation.

The hydro-monobenzoporphyrins are formulated into pharmaceutical compositions for administration to the subject or applied to an in vitro target using techniques known in the art generally. A summary of such pharmaceutical compositions may be found, for example in *Remington's Pharmaceutical Sciences*, Mack Publishing Co., Easton, Pa., latest edition.

The conjugates and hydro-monobenzoporphyrins of the present invention, labeled or unlabeled, can be administered systemically; in particular by injection, or can be used topically. The Gp or conjugates can be used singly or as components of mixtures.

Injection may be intravenous, subcutaneous, intramuscular, or even intraperitoneal. Injectables can be prepared in conventional forms, either as liquid solutions or suspensions, solid form suitable for solution or suspension in liquid prior to injection, or as emulsions. Suitable excipients are, for example, water, saline, dextrose, glycerol and the like. Of course, these compositions may also contain minor amounts of nontoxic, auxiliary substances such as wetting or emulsifying agents, pH buffering agents and so forth.

Systemic administration can also be implemented through implantation of a slow release or sustained release system, by suppository, or, if properly formulated, orally. Formulations for these modes of administration are well known in the art, and a summary of such methods may be found, for example, in *Remington's Pharmaceutical Sciences* (supra).

If treatment is to be localized, such as for the treatment of superficial tumors or skin disorders, the active conjugates or compounds may be topically administered using standard topical compositions involving lotions, suspension, or pastes. The topical formulations will contain typical excipients and are in the form of liquids, creams, gels or ointments. These formulations may also contain penetrants, such as DMSO and/or additional ingredients which affect depth of administration locally.

The quantity of conjugates or green porphyrin derivative to be administered depends on the choice of active ingredient, the condition to be treated, the mode of administration, the individual subject, and the judgment of the practitioner. Depending on the specificity of the preparation, smaller or larger doses may be needed. For compositions which are highly specific to target tissues, such as those which comprise conjugates of the green porphyrin with a highly specific monoclonal immunoglobulin preparation or specific receptor ligand, dosages in the range of 0.05-1 mg/kg are suggested. For compositions which are less specific to the target tissue, larger doses, up to 1-10 mg/kg may be needed. The foregoing ranges are merely suggestive, as the number of variables in regard to an individual treatment regime is large and considerable excursions from these recommended values are expected.

In addition to in vivo use, the compounds of the invention can be used in the treatment of materials in vitro to destroy harmful viruses or infectious agents. For example, blood plasma or blood which is to be used for transfusion or banked for future transfusion can be treated with the compounds of the invention and irradiated to effect sterilization. In addition, biological products such as Factor VIII which are prepared from biological fluids can be irradiated in the presence of the compounds of the invention to destroy contaminants. The photosensitizer is added to the sample in a concentration range dependent on the nature of the sample, but generally, for example, for blood amounts of 0.5-10 $\mu$g/ml of the photosensitizer are used. The biological sample is incubated with the photosensitizer for one to several hours, usually at room temperature, before exposure to light. The biological fluid in the presence of photosensitizer is then irradiated using an appropriate light source, such as a tungsten light bulb emitting over the range of the visible spectrum with light intensity of about 5-10 mW/cm$^2$, or LEDs with emission bands in the 600-800 nm range. The light from broad-spectrum sources is filtered so as to deliver the appropriate wavelength for absorption by the photosensitizer.

For use as a diagnostic in localizing tumor tissue or in localizing plaques, the compounds or conjugates of the invention are administered systemically in the same general manner as described above with respect to photodynamic therapy. The waiting period to allow the drugs to clear from tissues to which they do not home is approximately the same, about 30 minutes to 10 hours. After the compounds of the invention or their conjugates have been permitted to home, the location of the target tissue is determined by detecting the presence of the drug.

For diagnosis, the compounds or conjugates may be used along with, or may be labeled with, a radioisotope or other detecting means. If this is the case, the detection means depends on the nature of the label. Scintigraphic labels such as technetium or indium can be determined using ex vivo scanners. Specific fluorescent labels can also be used, but these require prior irradiation, as does the detection based on fluorescence of the compounds of the invention themselves.

For activation of the fluorescence of the compounds of the invention, any suitable absorption wavelength is used. This can be supplied using the various methods described above to provide cytotoxicity. Suitable detection means for the emitted visible radiation are then arranged, as exemplified, for example, in Example 15 hereinbelow. In a typical protocol, several hours before irradiation, approximately 0.5 mg/kg of the green porphyrin is injected intravenously and then excited by a wavelength of, for example, 630 nm, and the fluorescence is then read at, for example, 690 nm. Suitable devices for the detection of fluorescence are set forth in U.S. Pat. No. 4,649,151 and U.S. Ser. Nos. 502,447 filed Mar. 30, 1990 and 572,902 filed 24 August 1990, which are incorporated herein by reference. Detection and localization of plaques or tumors using the compounds of the invention can be combined with other detection methods, if desired. For example, ultrasound has been used for the detection of various tumors in situ (Dalla Palma, L., et al., *Acta Oncologics* (1989) 28:157-162).

EXAMPLES

The following examples are intended to illustrate the invention but not to limit its scope.

EXAMPLE 1

In Vitro Photosensitization by Green Porphyrins

Target cells were washed three times in serum-free medium (DME), counted and made up to a concentration of $10^7$ cells per ml.

For the "affinity" assay, in the dark, 100 μl of the target cell suspension and 100 μl of the test or control compound were mixed. "Labeling" was allowed to continue for one hour at 4° C., and labeled cells were washed in the dark three times with 3 ml medium each time and resuspended in fresh medium. The resuspended cells were then subjected to light exposure at 300–750 nanometers for 30 minutes.

In a "direct" assay the target cells were irradiated immediately upon addition of the test or control compound.

The effect of irradiation was estimated using methods appropriate to the target cells.

When human erythrocytes (RBCS) were used as target cells, the hemolysis caused by irradiation of control (hematoporphyrin, Hp) labeled and green porphyrin (Gp) labeled cells were estimated visually. The Gp used in this Example was the BPD-DB of FIG. 2 wherein $R^1$ and $R^2$ are carboethoxy. Repeated tests showed this green porphyrin to be 20-30 times more active than Hp in this assay. Thus, a concentration of 250 ng/ml Hp was required under the above conditions to obtain 50% hemolysis while only 10 ng/ml of green porphyrin was required to hemolyze 50% of the RBCs.

When the murine mastocytoma cell line P815 was used, the results were determined as follows:

The cells were labeled as above using concentration of 10–50 ng/ml of Hp as control and the BPD-DB as the test substance. The resuspended cells were treated with 300–750 nm light for 30 minutes and the viability resulting was estimated by direct counting using eosin-Y exclusion, a standard procedure for differentiating living from dead cells.

In other determinations conducted as above, the cells recovered from light exposure were assayed for viability by incubating them for 18 hours in 10 μCi/ml tritium-labeled thymidine according to the standard procedure whereby thymidine incorporation is equated with viability. The cells were harvested and radioactivity uptake was measured by a scintillation counter.

Fifty percent of the P815 cells were killed at 580 ng/ml Hp, but only 32 ng/ml green porphyrin (as BPD-DB) was required.

The results of each determination on a variety of cells is shown in Table 1 ($LD_{50}$ in the concentration of compound required to kill 50% of the cell population.)

TABLE 1

| Cell line | $LD_{50}$ (ng/ml) | | | |
| --- | --- | --- | --- | --- |
| | Direct test | | Affinity test | |
| | Gp | Hp | Gp | Hp |
| Normal lymphocytes | 4.2 | 31 | 11 | 100 |
| HL-60 | 3.5 | 64 | 7.2 | 145 |
| K562 | 70 | 770 | 33 | 2,500 |
| KG-1 | 163 | 960 | 80 | 2,350 |
| P815 | 32 | 580 | 26 | 1,300 |

EXAMPLE 2

Selective Binding of Green Porphyrin

P815 cells were incubated as described in Example 1 using 1–200 ng/ml Hp or Gp. The Gp was BPD-DB of FIG. 2 wherein $R^1$ and $R^2$ are carboethoxy. The cells were labeled in the dark for 30 minutes, washed free of unabsorbed porphyrins, resuspended, and then exposed to 300–750 nm light for another 30 minutes. Viability of the cells was established by tritiated thymidine incorporation after labeling with 20 μCi/ml tritiated thymidine and incubating at 37° C. for 18 hours.

The results showed that 50% of the P815 cells were destroyed at 6–20 ng/ml BPO-DB or at 200 ng/ml hematoporphyrin.

EXAMPLE 3

Preparation of Immunoconjugates

This example describes methods of preparation for immunoconjugates of four different antibody preparations with either hematoporphyrin (Hp) or green porphyrin (Gp); in this example, Gp is BPD-DB of FIG. 2 wherein $R^1$ and $R^2$ are carboethoxy. The antibodies employed were CAMAL-1, anti-M1 antibody, and B16G antibody, all prepared as described hereinabove, and affinity purified rabbit/antimouse Ig (RαMIg). In addition, a purified irrelevant monoclonal preparation (C-MAb) was used where a control was desired.

One preparation of the conjugates is basically as described in Mew, D., et al., *J Immunol* (1983) 130:1473 (supra). Briefly, to 220 mg pH 0.2 HCl (Sigma Chemical Co., St. Louis, Mo.) in 25 ml water and 0.8 ml N,N-dimethylformamide was added 20 mg 1-ethyl 3-(3-dimethylaminopropyl)-carbodiimide HCl (EDCI) in 0.6 ml water. After 30 minutes, this solution was mixed with 15 mg of the antibody protein dissolved in 5 ml distilled water and incubated for 5 hours. During this period, the pH of the solution was monitored and adjusted to between 6 and 7. Then 50 μl of monoethanolamine were added, and the solution was allowed to stand overnight at room temperature. The solution was dialyzed against 0.001 M phosphate buffer pH 7.4 for four days with three changes per day and overnight against PBS. The conjugate of green porphyrin is analogously prepared.

In a preferred method, the conjugation is conducted in an entirely nonaqueous solvent.

In a typical protocol, 2 ml of a dispersion in DMSO containing 5 mg each of the Hp or Gp and the dehydrating agent is prepared and stirred for 30 minutes at room temperature under nitrogen. To this is added a dispersion containing 2 mg of the appropriate immunoglobulin in 2 ml of DMSO, and the resulting mixture stirred for another 10 minutes. This mixture is then worked up by dilution in phosphate-buffered saline, pH 7.4 (PBS) by adding 5 times the volume of PBS containing 50 μl monoethanolamine, and is then dialyzed against PBS using three changes of wash.

Alternatively, 2 ml of a dispersion containing 5 mg each of Hp or Gp, a linking agent, and a dehydrating agent is prepared and stirred for approximately 15 minutes at room temperature under nitrogen. To this is then added a dispersion containing about 2 mg of the immunospecific protein in 2 ml of tetrahydrofuran and the resulting mixture stirred for another 10 minutes. The mixture is then worked up as described above.

The foregoing procedures are appropriate for CAMAL-1 and for the remaining antibody preparations above listed.

In addition, the following preparations were made specifically with B16G and RαMIg:

B16G 11 mg of hematoporphyrin plus 11 mg EDCI in 4 ml spectral grade DMSO was stirred for 30 minutes under nitrogen at room temperature before the addition of 20 mg lyophilized B16G antibodies, prepared as described by Maier, T., et al., *Immunol* (1983) 131:1843, in 2 ml DMSO. The resulting mixture was stirred for 40 seconds at room temperature and worked up as described above. The resulting product contained 375 mg Hp/mg B16G. A similar procedure is used substituting Gp for Hp.

RαMIg 400 mg of EDCI and 400 mg hematoporphyrin in 1 ml DMSO were stirred for 30 minutes under nitrogen at room temperature as above before the addition of 800 μg lyophilized RαMIg antibodies, prepared as described by Mew, D., et al., *J Immunol* (1983) 1473-1477, in 1 ml DMSO. The resulting mixture was stirred for 30 seconds and worked up as described above to obtain a product containing 200 μg Hp/mg RαMIg. A similar procedure is used substituting Gp for Hp.

EXAMPLE 4

Specificity of Immunoconjugates in Vitro

In the following determinations, the levels of antibody conjugation were as follows, expressed as Ag Hp or green porphyrin (Gp) per mg immunoglobulin:
RαMIg-Hp: 110 μg/mg;
B16G-Hp, 156 μMg/mg;
CAMAL-1-Hp, 260 μg/mg;
Anti-M1-Hp, 170 μg/mg;
C-MAb-Hp, 95 μg/mg;
RαMIg-Gp, 120 μg/mg;
B16G-Gp, 165 μg/mg;
B16G-1-Gp, 75 #g/mg;
C-MAb-Gp 90 μg/mg The Ig-Hp and Ig-Gp conjugates are tested against cells in vivo by mixing the conjugates with the appropriate cell types, along with suitable controls, and then exposing the labeled cells to irradiation. Procedures for carrying out this assay were described in detail in Mew, D., et al., *Cancer Research* (1985), for CAMAL-1, and by Mew, D., et al., *J Immunol* (1983), for Anti-M1, both references cited hereinabove and incorporated herein by reference.

Briefly, for CAMAL-1, three cell lines, WC4, WC6 and WC2 (WC4 and WC6 produces the CAMAL antigen, but WC2 does not), are labeled with the appropriate Ig-Hp or Ig-Gp preparation as described above in Example 1. The labeled cell preparations containing $10^6$ cells each are introduced to Rose chambers and exposed to light activation with a laser at 630 nm. The results for various preparations are then compiled.

For the anti-M1 conjugate, M1 tumor cells are used as target cells and treated with the Ig-Hp, Ig-Gp conjugates or drug or antibody alone or the combination of antibody and drug, but uncoupled, by incubating them in 6% $CO_2$ humidified incubator at 37° for two hours. The cells are washed three times in PBS and then plated and exposed to fluorescent light overnight. The cells are assessed for viability by tritiated thymidine uptake as above.

For the B16G conjugates, A10, P815, and L1210 cells are used as target cells. (A10 cells are a T-cell hybridoma which secretes a B16G-reactive T suppressor factor; P815 cells are also reactive with B16G.) The in vitro study is done using a direct method employing the B16G-Hp or B16G-Gp conjugate or indirectly using unlabeled B16G antibodies and labeled RαMIg-Hp or RαMIg-Gp.

In a direct method, $5 \times 10^5$ cells are suspended in 1 ml DME/Hepes containing the appropriate Ig-drug conjugate as test or control at Hp or Gp concentrations of 320, 160, 80, 40 and 20 ng drug/ml. The cells are incubated in the dark at 37° for one hour, then washed three times in 5 ml DME/Hepes and then resuspended in 1 ml of the same buffer. Three 100 μl test portions of the labeled preparations are dispensed into flat bottom microtiter wells and the remainder of the cell suspensions (700 μl) are exposed to incandescent light (22.5 mW/cm$^2$) at a distance of 20 cm for one hour. Then three additional 100 ml aliquots are removed to microtiter wells. Tritium-labeled thymidine diluted in DME/Hepes containing 20% FCS is then added to all microtiter wells in 100 ml aliquots so that 2 μCi of labeled thymidine is added to each well. Cultures are incubated for 18 hours at 37° C. and humidified 10% $CO_2$ and then harvested on a MASH harvester. Thymidine incorporation was measured with an Hp scintillation counter (Tri-Carb Model 4550). The results of this study for Ig-Hp are shown in Table 2.

TABLE 2

| | % killing of cell lines | | |
|---|---|---|---|
| | A10 | P815 | L1210 |
| B16G Hp (ng Hp/ml) | | | |
| 320 | 100 | 70 | 55 |

TABLE 2-continued

| | % killing of cell lines | | |
|---|---|---|---|
| | A10 | P815 | L1210 |
| 160 | 100 | 50 | 10 |
| 80 | 100 | 20 | 0 |
| 40 | 65 | 10 | 0 |
| 20 | 20 | 0 | 0 |
| C-Mab-Hp (ng Hp/ml) | | | |
| 320 | 63 | 75 | 50 |
| 160 | 35 | 48 | 15 |
| 80 | 0 | 25 | 0 |
| 40 | 0 | 12 | 0 |
| 20 | 0 | 0 | 0 |

In an indirect assay, the A10 suspended cells, prepared as described above, are exposed to 50 μg/ml of either B16G or a control antibody C-MAb at 4° C. for 30 minutes, washed in DME/Hepes, and then exposed for an additional 30 minutes at 4° C. in the dark to varying concentrations of RαMIg-Hp or RαMIg-Gp between 2 μg/ml and 15 ng/ml of Hp or Gp. The cells are assessed for viability using labeled thymidine uptake as described above. These results for Ig-Hp are shown in Table 3.

TABLE 3

| RαMIg-Hp | Primary antibody | |
|---|---|---|
| (ng/ml) | B16G | C-MAb |
| 500 | 100 | 30 |
| 250 | 85 | 22 |
| 125 | 75 | 5 |
| 52.5 | 60 | 2 |
| 31.2 | 47 | 3 |
| 15.6 | 18 | 1.5 |

Similar results are obtained using corresponding conjugates with Gp.

EXAMPLE 5

In Vivo Cytotoxicity of the Immunoconjugates

The efficacy of the conjugates and of the Gp compounds of the invention in vivo is also assessed. For the CAMAL-1 and anti-M1 conjugates, the procedures are as described in the two Mew et al. papers referenced above in Example 4. The Gp compound alone shows superior results at appropriate wavelengths as compared to the Hp labeled conjugates.

For the B16G-Hp or B16G-Gp conjugates and for the Gp (BPD-DB) alone, the in vivo studies are conducted as follows:

The in vivo test relies on the indirect effect of a population of T-suppressor cells on tumors, which then serve as means to assess the effectiveness of the irradiation treatment. P815 mastocytoma cells grown in syngeneic DBA/2 mice stimulate T-suppressor cells specific for the tumor. These T-suppressor cells impede the development of specific T-killer cells which would otherwise aid in the regression of the tumor. The T-cell hybridoma designated A10 above secretes a T-suppressor factor which is associated with these T-suppressor cells. Thus, selective killing of these T-suppressor cell populations through reaction with conjugates in which the Ig is an antibody specific for the T-suppressor factor on the surface of the cells (namely B16G) should result in tumor regression in mice bearing the P815 tumors.

Therefore, in this assay, DBA/2 mice are injected in the right flank subcutaneously with $10^4$ P815 cells to incorporate the tumor. On day eight, when the tumors are palpable (approx. 25-42 sq mm) the mice are randomly sorted into groups of eight and injected IV with 150 μl PBS containing nothing, Hp or Gp, B16G-Hp or B16G-Gp, B16G plus either drug, B16G alone or C-MAbHp or C-MAb-Gp. The levels of Hp are 50 Mg per animal in all cases and B16G 310 μg in all cases (where appropriate).

The animals are maintained in the dark for two hours and then exposed to strong light at 300-750 nm and 22.5 mW/cm². The animals were then treated normally and monitored on a daily basis.

Animals treated with B16G Hp survived and were tumor free after 100 days. Results obtained are shown in Table 4.

TABLE 4

| Experiment | Treatment | Mean survival time (days) | No. of cures | % tumor-free after 100 (days) |
|---|---|---|---|---|
| 1 | PBS | 25.0 | 0/7 | 0 |
| | B16G-Hp | 41.3 | 3/9 | 33 |
| 2 | PBS | 23.5 | 0/6 | 0 |
| | Hp | 21.0 | 0/8 | 0 |
| | B16G-Hp | 24.2 | 3/8 | 37.5 |
| 3 | PBS | 24.1 | 0/7 | 0 |
| | Hp | 23.4 | 0/7 | 0 |
| | B16G + Hp | 23.5 | 0/6 | 0 |
| | B16G-Hp | 29.2 | 2/7 | 29 |
| 4 | PBS | 25.2 | 0/8 | 0 |
| | B16G | 28.3 | 0/8 | 0 |
| | Hp | 24.2 | 0/8 | 0 |
| | B16G + Hp | 24.6 | 0/7 | 0 |
| | B16G-Hp | 36.7 | 3/7 | 43 |
| 5 | PBS | 23.8 | 0/8 | 0 |
| | Hp | 27.0 | 0/8 | 0 |
| | C-MAb-Hp | 20.3 | 0/8 | 0 |
| | B16G-Hp | 34.0 | 1/8 | 12.5 |

Similar results are obtained for Gp alone or Gp conjugates.

EXAMPLE 6

In Vitro Evaluation of BPD-DA, -MA, -DB and -MB

The four compounds shown in FIG. 2, wherein $R^1$ and $R^2$ are carbomethoxy, were tested in vitro as described in Example 1. All four compounds were photosensitive; the monoacid forms BPD-MA and BPD-MB were somewhat more active.

EXAMPLE 7

Biodistribution and Degradation

Biodistribution studies have been conducted using tritiated BPD-MA and BPD-MB. Table 5 shows the ratios between $^3$H-BPD-MA concentration in the tumor and in normal tissues determined at various times post-injection in mice bearing P815 tumor as the average for 3 mice.

TABLE 5

| | Time Post Injection | | | | | |
|---|---|---|---|---|---|---|
| Tissue | 3 h | 24 h | 48 h | 72 h | 96 h | 168 h |
| Blood | 0.52 | 1.45 | 1.37 | 1.66 | 2.77 | 3.65 |
| Brain | 3.76 | 3.06 | 2.92 | 2.69 | 4.18 | 6.91 |
| Heart | 1.09 | 1.71 | 1.63 | 1.46 | 2.24 | 2.51 |
| Intestine | 2.42 | 1.85 | 1.88 | 1.48 | 3.29 | 2.23 |
| Lung | 0.79 | 1.55 | 1.47 | 1.16 | 1.63 | 1.79 |
| Muscle | 2.68 | 2.98 | 2.77 | 2.16 | 3.45 | 4.23 |
| Skin | 2.57 | 1.64 | 1.95 | 1.57 | 2.03 | 3.51 |
| Stomach | 1.57 | 1.89 | 2.08 | 2.04 | 2.23 | 2.98 |

Tumor skin ratios are most favorable 3 hours after IV administration of the drug.

To determine biodegradability, tritiated BPD-MA was injected IV into P815 tumor-bearing mice. The mice were sacrificed at either 3 or 24 hours following injection and tumors, livers and kidneys were removed. The BPD-MA in these tissues was extracted and photoactivity was assessed in P815 target cells as described above in Example 1 under standard in vitro conditions. While 100% of BPD-MA in tumor was active at 3 hours, only 39% was active at 24 hours; both the liver and kidney degraded BPD more rapidly than did tumor tissue. Administration of tritiated BPD-MB in the same system gave similar results.

Similar studies using BPD-MA conjugated to an antikeratin Mab in a model murine system carrying the KLN squamous tumor cell line showed improved concentration of the drug in the target tissue.

EXAMPLE 8

In Vivo Photosensitization by BPD

Studies of potential photosensitizers were performed using the M-1 rhabdomycoscercoma system in DBA/J2 mice. The compositions to be tested were diluted to a concentration of 800 mg/ml in PBS from a stock solution in DMSO at 8 mg/ml (except Photofrin® II, which was diluted directly from the clinical vial). Animals (8 per group) received 0.1 ml (80 mg) of material IV 24 h prior to exposure to light, provided by a 150W tungsten bulb, red filter (transmits light >600 nm), hot mirror (reflects light >720 nm) and 2 fiber optics, at 567 Jo/cm$^2$.

The results, shown in Table 6, indicate all BPD compounds tested gave positive results. The superior results shown by Photofrin® II compositions are explainable by the observation that initial tumor sizes were smaller (a result of chance).

TABLE 6

| Photosensitizer | Days Tumor Free (PR) | Number of Cures* | Tumor Volume at Time of Light Treatment (mm$^3$) |
|---|---|---|---|
| None | 0.5 | 2 | 22.4 ± 7.8 |
| Photofrin® II composition | 21.3 | 5 | 11.9 ± 6.9 |
| BPD-MA | 9.2 | 4 | 19.0 ± 13.0 |
| BPD-MB | 10.6 | 3 | 18.2 ± 11.0 |
| BPD-DA | 10.7 | 4 | 18.7 ± 9.9 |
| BPD-DB | 10.6 | 3 | 25.4 ± 16.4 |

*Animals whose tumors regressed and who remained tumor-free for 30 days.

Similar studies, except using a light dose of 378 To/cm$^3$, resulted in the out come shown in Table 7.

TABLE 7

| Photosensitizer | Number of Animals | Days Tumor-free | Number of Cures |
|---|---|---|---|
| None | 11 | 0.1 | 2 |
| Photofrin® II | 10 | 9.5 | 4 |
| BPD-MA | 10 | 13.2 | 4 |
| BPD-MB | 9 | 8.7 | 6 |
| BPD-DA | 15 | 2.5 | 4 |
| BPD-DB | 13 | 13.0 | 8 |

The foregoing results are preliminary, and the assay protocols have not yet been optimized.

EXAMPLE 9

Alternate In Vivo Assay

Mice bearing small tumors were injected IV with drug to be tested. Three hours later the animals were sacrificed and their tumors removed. The tumor cells were teased apart to form a single cell suspension, and the cells were plated at 10$^5$/well and exposed to light at a prescribed dose. The plates were incubated overnight and assayed for viability by MTT assay.

The results of one study are shown in Table 8.

TABLE 8

| Photosensitizer | Dose (μg/mouse) | Light Dose (Jo) | % Kill |
|---|---|---|---|
| BPD-MA | 33 | 5.7 | 22.0 |
|  | 40 | 3.8 | 32.5 |
|  | 80 | 3.8 | 63.5 ± 2.1 |
|  | 80 | 3.8 | 53.7 ± 6.2 |
| BPD-MB | 33 | 5.7 | 25.2 |
| BPD-DA | 80 | 3.8 | 11.0 |
|  | 80 | 7.6 | 26.0 |

Thus, the BPD forms tested were active in this assay; it appears light intensity and drug levels are subject to optimization and correlation.

EXAMPLE 10

Comparison of BPD to Photofrin® II Compositions

Figures 1, 2, 3, 4:
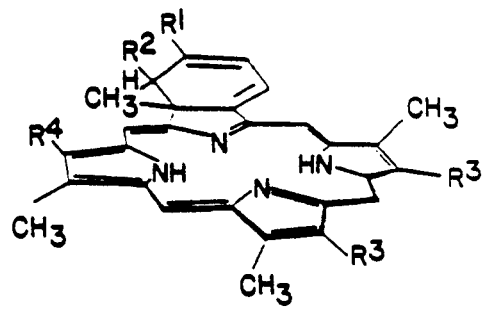
FIG. 4 shows the results of skin sensitivity assay using a BPD compound.

Mice bearing P815 tumors were shaved and injected with equivalent amounts of photosensitizer, and exposed to 72 Jo/cm$^2$ (80 mw/cm$^2$-15 min-full spectrum) at various time intervals. Skin biopsies were taken at 24 and 48 hours after light irradiation and visual evaluations were made blind. The results of these evaluations are shown in FIG. 4. BPD-MA and, to a lesser extent, BPD-MB had major photosensitizing activity, under these conditions; this was o1 '  present when light treatment was given 3 hours pos drug administration, consistent with the biodegradability of these compounds.

EXAMPLE 11

Preparation of Compounds of the Invention

The following compounds have been prepared using the above-described Diels-Alder reaction of MeOOC—C≡C—COOMe with the dimethyl ester of protoporphyrin IX, followed by rearrangement to the forms shown as formulas 3 and 4 of FIG. 1 and by subsequent treatment to hydrolyze or modify the propionic ester on rings C and D and/or to modify the unreacted vinyl group on the A or B ring remaining after the Diels-Alder reaction with the B or A ring, as the case may be. The products are compounds of the following formulas, wherein R" is OR* or NR* wherein R* is alkyl, alkylene, or H (or an organic or unorganic cation):

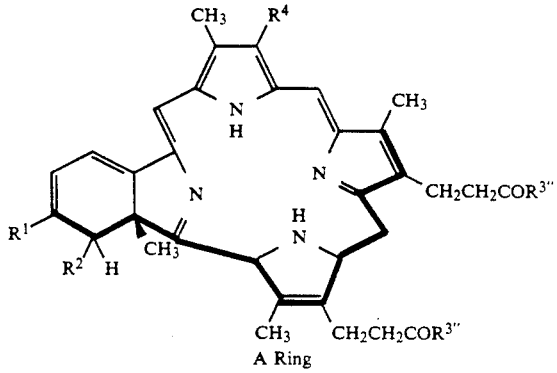

A Ring

-continued

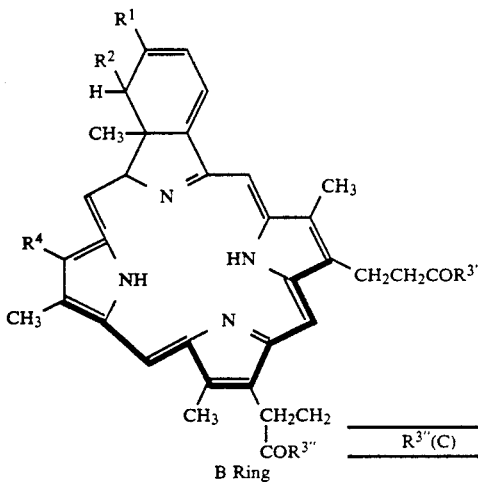

B Ring wherein R¹ and R² are, in all cases, COOMe.
The compounds prepared are as follows:

| | R³″(C) | R³″(D) | R⁴ |
|---|---|---|---|
| | | | A-Ring |
| 1. | OMe | OMe | CHCH₂ |
| 2. | OH | OMe | CHCH₂(BPD-MA) |
| 3. | OMe | OH | CHCH₂(BPD-MA) |
| 4. | OH | OH | CHCH₂(BPD-DA) |
| 5. | OMe | OMe | CH(NH₂)Me |
| 6. | OMe | OMe | CH(NHCO-C₆H₄-NO₂)Me |
| 7. | OH | OH | CH(NHCO-C₆H₄-NO₂)Me |
| | | | B-Ring |
| 1. | OMe | OMe | CHCH₂ |
| 2. | OH | OMe | CHCH₂ |
| 3. | OMe | OH | CHCH₂ |
| 4. | OH | OH | CHCH₂ |
| 5. | OMe | OMe | CH(NH₂)Me |
| 6. | OH | OH | CH(NH₂)Me |
| 7. | OMe | OMe | CH(NH(CH₂)₆NH₂)CH₃ |
| 8. | OH | OH | CH(NH(CH₂)₆NH₂)CH₃  9. OCD₃ |
| | OCD₃ | CH(NH(CH₂)₆NH₂)CH₃ | |
| 10. | OMe | OMe | CH(imidazolyl)CH₃ |
| 11. | OMe | OMe | CH(NHCO-C₆H₄-maleimidyl)Me |
| 12. | OMe | OMe | CH(NHCO-C₆H₄-N-succinimidyl-S(CH₂)OH)CH₃ |
| 13. | OMe | OMe | CH(OH)Me |
| 14. | OMe | OMe | CHBrMe |
| 15. | OMe | OMe | CH(OMe)Me |
| 16. | OMe | OMe | CH(pyridinium Br)Me |
| 17. | NH(CH₂)₆NH₂ | OMe | CHCH₂ |
| 18. | R³″—R³″—NH(CH₂)₆NH— | | CHCH₂ |
| 19. | OMe | OMe | CH(SH)CH₃ |
| 20. | OMe | OMe | disulfide of above |
| 21. | OMe | OMe | CHO |
| 22. | OMe | OMe | CHOHCH₂OH |

EXAMPLE 12

Preparation of BPD Dimer-Vinyl Linked

To a stirring solution of BPD-DB (wherein $R^1=R^2=$ carbomethoxy and which is esterified so that both $R^3$ are carbomethoxyethyl) (35 mg, 48 μmol) in 5 ml of dichloromethane cooled to dry ice/acetone temperature was added trifluoromethane sulfonic acid (34 μl, 380 μmol). An oil separated out upon the addition of the acid. The reaction was brought up to 0° C. Then 5 ml of 5% sodium bicarbonate was added to the reaction to neutralize the acid. The product distributed into the organic layer which was washed three times with water. The solvent was removed and the product was dried via azeotrope with acetonitrile.

Preparative thin layer chromatography on silica gel eluting with 10% ethylacitate/dichloromethane gave a single fraction (28 mg, 80% yield). Parent ion in mass spectrum was 1464. The complex proton NMR due to the number of isomeric compounds had the characteristic single vinyl hydrogen associated with a C-linkage at about 8.1 ppm.

EXAMPLE 13

Elimination of Viral Contaminants From Blood

Whole blood was obtained from the Canadian Red Cross as units of donor blood. VSV, which was cultured in VHK and VERO cell lines to obtain a stock viral concentration of $4 \times 10^8$ plaque-forming units (pfu)/ml, was added the blood at a concentration of $10^7$ pfu/ml. The virus-infected blood was tested using the neutral red dye uptake assay described by Finter, N. B., *J Clin Virol* (1969) 5:419–425, to establish that, over a 6-hour period, no significant nonspecific elimination of active virus occurred.

VSV-spiked blood was dispensed in 1 ml aliquots into 6-well plates and, under reduced light conditions, varying concentrations of either BPD-MA or BPD-MB were added. The photosensitizers were maintained as stock solutions of 8 mg/ml in dimethyl sulfoxide (DMSO) at −20° C. They were thawed and diluted immediately before use into phosphate-buffered saline (PBS) before addition to the blood. BPD-MB required a 20-minute sonication in ultrasonic bath to achieve solubility.

The samples were incubated for various time periods in the dark before exposure to light, which was provided in a light box containing 16 100W tungsten light bulbs (GE 400–1200 nm). The light passed through a 4-cm thick chamber filled with circulating cooled water covered by a matted glass plate to disperse the light and to give a light intensity of 8 mw/cm$^2$ as measured by a Gentec Model TPM Radiometer. The 6-well plates containing the blood samples were placed on top of the matted glass plate and exposed for varying lengths of time.

After treatment, the virus concentration in the blood samples was determined by the neutral red dye uptake assay (Finter (supra)). Briefly, 96-well flat-bottom plates were inoculated with VERO cells and grown to near confluency. Starting at 1:50, fivefold dilutions of the treated blood samples were added in quadruplicate to the VERO monolayers. After 48 hours of incubation at 37° C. in 5% $CO_2$, the plates were washed twice with PBS and neutral red dye was added and incubated for 45 minutes. Excess dye was washed off before addition of lysing buffer. The color intensity of the dye taken up and retained by viable cells was then measured as absorbance units at 492 nm.

The results of the neutral red dye assay were verified and correlated with viral destruction by a standard plaque assay in which dilutions of treated blood were added (0.1 ml) in duplicate to VERO monolayers in 6-well plates. After 1 hour of incubation at 37° C. plus 5% $CO_2$ the monolayers were washed twice with PBS and overlaid with 0.8% agar in DMEM and plaques were counted after 24 hours.

Parameters for treatment were determined using the foregoing protocol. BPD-MA was added at 1, 2 and 4 μg/ml to 1 and 2 ml of VSV-spiked blood samples and the samples were incubated in the dark for 2 hours at room temperature before exposure to 57.6 J/cm$^2$ of light. In all samples, the addition of 2 and 4 μg/ml BPD-MA resulted in complete virus inactivation, but at 1 mg/ml, a 4 log virus kill was seen in the 1 ml sample, as compared to only a 2 log virus kill in the 2 ml sample. The results show that the blood sample must be sufficiently exposed to the light source to effect the photosensitization. Consistent with this, when 1 ml samples were spiked with 1, 2 and 4 μg/ml BPD-MA for 2 hours before light exposure for various times, the resulting data showed an inverse relationship between total light energy and the drug dose required to inactivate the VSV. Furthermore, VSV inactivation by BPD-MA at 1 μg/ml was dramatically improved by increasing light intensity from 28.8 to 57.6 J/cm$^2$. Exposure to 57.6 J/cm$^2$ resulted in 5 logs of kill, as opposed to 2 logs of kill at the lower intensity.

The effect of incubation time prior to light exposure was also tested using 1 μg/ml BPD-MA at room temperature and incubating at 0.5, 1, 2 and 3 hours before exposure to light of 57.6 J/cm$^2$. Increase of the drug incubation time from 0.5 hour to 1 hour resulted in improved VSV inactivation, but further increases to 2–3 hours had little effect. Also, little difference was found when BPD-MA was incubated before light exposure at either room temperature, 37° C. or 4° C.

Finally, the assay was run under standard conditions using 1 ml samples of VSV-spiked blood treated for 2 hours with various concentrations of BPD-MA, BPD-MB or commercially available Photofrin® composition prior to light exposure at 57.6 J/cm$^2$. Under these conditions, 2 μg/ml BPD-MA resulted in a 7 log viral kill, 2 μg/ml BPD-MB resulted in 4 logs viral kill, and Photofrin® photosensitizer at even 40 mg/ml did not appear to kill the virus.

Distribution studies showed that approximately 20% of the VSV added to the samples were associated with the red blood cells, and that cell-associated VSV particles were inactivated to the same degree as free virus.

Under the conditions of the assay, the photosensitizer resulted in little, if any, lysis of the contained red blood cells.

EXAMPLE 14

Accumulation of BPD in Atherosclerotic Plagues

A. Pig Study

A formulation of BPD-MA was prepared by dissolving 8 mg BPD-MA in 1 ml of DMSO and diluting the resultant 9:1 with normal saline (NS). The resulting solution was administered intravenously at a dosage of 2 mg/kg to two of three farm swine which previously underwent iliofemoral artery denudation and had been maintained on a high cholesterol fat diet.

Three hours after the administration of the drug, the animals were euthanized and various tissues harvested, including plaque vessel, aorta, heart, kidney, liver, lung, muscle and skin. The tissues were assayed fluorometrically, including using fluorescence microscopy. The results showed that of the two pigs administered BPD-MA, the pig which had a high development of plaque disease showed higher accumulation of the BPD-MA; highest levels were in the lungs, but it was possible to distinguish between plaqued arteries and unplaqued arteries.

B. In Vitro Human Tissue Study

Human atherosclerotic iliofemoral arteries and aorta were harvested and wrapped in saline-soaked gauze and then incubated for 2 hours at room temperature in MEM-Eagle's Medium and 10% fetal calf serum mixed with BPD-MA formulated at 30 μg/ml. The BPD was prepared by mixing 1 ml of BPD-MA stock solution with 8.1 ml MEM-Eagle's Medium and 0.9 ml fetal calf serum.

The sample was rinsed three times in cold normal saline, and the sections were examined by fluorescence microscopy to evaluate the uptake of BPD. The administered dose was finally diluted to provide solutions containing 0.5-200 μg/ml, and incubation time was varied. The results showed that incubations performed with 10 μg/ml of BPD-MA or less did not provide sufficient fluorescence to detect the presence of plaques using fluorescence microscopy; however, at 100 μg/ml and above, fluorescence was clearly seen. When approximately 25 μg/ml were used in the incubation, BPD-MA showed most intensely in the plaqued areas, while no fluorescence was seen in the underlying arterial wall.

C. Rabbit Studies

In vivo studies were conducted in rabbits which did and did not contain atherosclerotic aortas. The rabbits were injected with BPD-MA at various dosages and time intervals prior to sacrifice. The rabbits were euthanized by injection and the entire descending aorta was removed, sectioned, and examined by fluorescence microscopy. No fluorescence was seen in tissue samples from rabbits receiving 30 μg/kg BPD-MA dosages; however, at 100 μg/kg, whereas no fluorescence was shown in the normal aorta samples, in the two atherosclerotic samples, fluorescence was seen in the plaque but not the arterial wall.

EXAMPLE 15

Detection of Tumors Using BPD-MA

BPD-MA was dissolved in DMSO and diluted with phosphate-buffered saline to a neutral pH and intravenously injected at a dose of 3.5 mg/kg body weight to white inbred male Wistar/Furth rats weighing about 240 g which had ten days previously been subcutaneously inoculated in both hind legs with syngeneic tumor cells prepared from a colon adenocarcinoma. The rats were sacrificed three hours later and the tumors localized through the mediation of the drug.

Fluorescence measurements were made using a fiber optic fluorosensor, as described in Andersson Engels, S., et al. *Lasers in Med Sci* (1989) 4:241. A pulsed nitrogen laser (Laser Science Model VSL-DCM-3) was used as an excitation source. The laser emits light at 337 nm and every pulse is about 3 ns long at 10 Hertz with a pulse energy of about 175 μJ. The light is transmitted through an optical fiber; the same fiber collects the fluorescent light which is pulsed through a polychromator with a wavelength resolution of 25 nm. A detector is placed in the focal plane of the polychromator. The detector is an EG & G Parc Gatable Image-Intensified 1024-Element Diode Array Detector, Model 1421. The fluorescence signal is detected in the 300–800 nm wavelength range.

The fluorescence spectrum of the emitted light corresponds to that of BPD-MA. When scanned across a tumor area with surrounding nondiseased tissue, the BPD-MA-related signal increases over the malignant tumor. In general, the exterior portion of the tumor, 3 hours after intravenous injection, has a higher fluorescence than the interior part of the tumor and about 2.5 times higher intensity than the surrounding muscle. Liver also shows a high fluorescence intensity, while kidney and spleen exhibit low values; the urinary bladder is about the same intensity as the kidney, and the urine has higher fluorescence The stomach and small intestine have higher intensity than the more distal part of the gastrointestinal system, and the feces show very low intensity. The organs in the respiratory/circulatory system and skin also have a low uptake.

The performance of BPD-MA in the detection assay is comparable to that of the known porphyrin-detecting drugs. Specifically, the ratio of the tumor exterior to muscle for BPD-MA is approximately the same as that for HP; however, DHE shows a tumor-to-muscle ratio of 6:1, polyhematoporphyrin ester shows 5.5:1, and tetrasulfonated thalocyanine shows a ratio of about 3:1.

EXAMPLE 16

Effect of Systemic Administration on Papilloma-Caused Warts

Rabbits displaying warts caused by Papilloma virus were provided according to the model described by Shope et al., *J. Exp. Med,* (1933) 58:607–624. Five rabbits were administered Photofrin ® II porfimer sodium intravenously at 10 mg/kg total dose over a ≦5 minute period beginning 24 hours before irradiation treatment. Six rabbits were administered BPD-MA intravenously at 2 mg/kg total dose over a ≦5 minute period beginning 2.5–3.5 hours before irradiation treatment. Warts were irradiated individually with no light, 150 J/cm$^2$ or 250 J/cm$^2$ using 630 nm for porfimer sodium and 690 nm for BPD-MA. Controls with no light irradiation did not show regression.

For 10 warts irradiated at 150 J/cm$^2$ in porfimer Na-treated animals, 8 completely regressed and another showed >50% regression; for 10 warts irradiated at 250 J/cm$^2$, 8 completely regressed and 2 showed >50% regression.

For 12 warts irradiated at 150 J/cm$^2$ in BPD-MA-treated animals, 7 completely regressed and 5 showed >50% regression; for 12 warts irradiated at 250 J/cm$^2$, all 12 showed complete cure.

EXAMPLE 17

Topical Treatment of Papilloma-Caused Warts

The efficacy of porfimer Na and BPD-MA applied topically was studied in the rabbit papilloma virus model of Example 16.

The topical formulations employed were as follows:
1. Photofrin/OAP: 24 mg porfimer sodium per ml vehicle (oleic acid, 23%; ethanol, 46%; propylene glycol, 23%; laureth-9, 8%; and polyvinyl pyrrolidone K-90, 20 mg/ml).

2. Photofrin/OB: 39 mg porfimer sodium per ml vehicle (oleyl alcohol, 25%; ethanol, 50%; propylene glycol, 25%; benzalkonium chloride, 5 mg/ml; polyvinyl pyrrolidone, 20 mg/ml).

3. BPD/Pharmasolve: 10 mg BPD-MA per ml Pharmasolve.

4. BPD/DMSO: 10 mg BPD-MA per ml DMSO.

5. BPD/OA: 10 mg BPD-MA per ml vehicle (a proprietary formulation containing oleic acid in an alcohol base, developed by American Cyanamid).

6. BPD/OL: 10 mg BPD-MA per ml vehicle (a proprietary formulation containing oleyl alcohol in an alcohol base, also developed by American Cyanamid).

Each wart was topically treated 3 hours before irradiation with either 150 J/cm$^2$ or 250 J/cm$^2$ at 630 nm for porfimer Na formulations and 690 nm for BPD formulations.

Photofrin/OAP showed little effect on the warts at either energy; photofrin/OB gave complete regression for 1 of 9 warts at 150 J/cm$^2$ and 2 of 8 warts at 250 J/cm$^2$; the remaining warts showed >50% regression in each case. The results for BPD formulations are shown in Table 9.

ered (occluded) to prevent evaporation, and the experiment was conducted in the dark.

Six diffusion cells were run for each time point (1.5 hr, 3 hr, 24 hr) for each formulation. Samples were removed from the dermal chamber at 1.5 hr, 3 hr and 24 hr. Cumulative penetration was assayed by liquid scintillation.

At the end of the respective time point, the surface of the skin was washed to remove surface drug. A 4 mm full thickness skin punch biopsy was taken from each specimen and processed for frozen section tissue fluorescence. This necessitates termination of flux measurements in that chamber. The stratum corneum was removed by 25 repetitive strippings with cellophane tape and counted in groups of five. The epidermis was heat-separated from the dermis by heating to 60° C. for 1 minute. These tissues were then digested and the $^{14}$C-BPD content of each of the skin compartments and reservoir was determined by liquid scintillation counting. Results are set forth in Tables 10 and 11. (In the tables, "BPD-OA" and "BPD-OL" represent the BPD-oleic acid and BPD-oleyl alcohol formulations of the preceding example, "CH-014" represents $^{14}$C-labeled BPD-MA, and "phospholipid" represents a BPD-MA liposomal formulation.)

TABLE 10

| | PERCENT RECOVERY | | | | | |
|---|---|---|---|---|---|---|
| TIME (HRS): | 1.5 | 3 | 24 | 1.5 | 3 | 24 |
| | Stratum Corneum | | | Epidermis | | |
| BPD-OA | 15.5 ± 11.4 | 16.6 ± 1.8 | 11.6 ± 7.5 | .12 ± .04 | .10 ± .03 | .08 ± .09 |
| BPD-OL | 4.9 ± 1.6 | 16.1 ± 10.2 | 11.1 ± 5.0 | .08 ± .03 | .12 ± .04 | .05 ± .02 |
| CH-014 | | | | .13 ± .13 | .06 ± .02 | .06 ± .03 |
| Phospholipid | | | | .21 ± .13 | .28 ± .13 | .24 ± .19 |
| | Dermis | | | Reservoir | | |
| BPD-OA | .34 ± .10 | .37 ± .07 | .36 ± .17 | 0 | .01 ± .01 | .08 ± .03 |
| BPD-OL | .25 ± .10 | .30 ± .12 | .25 ± .08 | 0 | 0 | .11 ± .06 |
| CH-014 | .19 ± .06 | .32 ± .11 | .40 ± .28 | 0 | 0 | .014 ± .018 |
| Phospholipid | .48 ± .14 | .62 ± .36 | .30 ± .12 | 0 | 0 | .014 ± .002 |

TABLE 9

| | Regresssion | | | | | |
|---|---|---|---|---|---|---|
| | 100% | | >50% | | <50% | |
| Formulation | 150J | 250J | 150J | 200J | 150J | 250J |
| BPD/Pharmasolve | 2/4 | 2/4 | 0/4 | 0/4 | 2/4 | 2/4 |
| BPD/DMSO | 0/2 | 0/2 | 1/2 | 0/2 | 1/2 | 2/2 |
| BPD/OA | 5/5 | 6/6 | 0/5 | 0/6 | 0/5 | 0/6 |
| BPD/OL | 5/7 | 4/8 | 2/7 | 4/8 | 0/7 | 0/8 |

Thus, BPD, when properly formulated, is effective in causing regression applied topically to warts.

EXAMPLE 18

In Vitro Skin Penetration Studies

Franz in vitro percutaneous diffusion chambers were used to conduct studies of BPD formulations with oleic acid and oleyl alcohol vehicles ($^{14}$C-BPD having a specific activity of 6 μCi was used). Excised split thickness (200 μ) human cadaver skin was mounted on the chamber (surface area 3 cm$^2$). The lower reservoir contained 4% bovine serum albumen in isotonic buffered saline, pH 7.0.

The chambers with the skin were equilibrated to 37° C. prior to application of the drug formulations. Formulations (0.25 containing 1.67 μCi) were applied to the epidermal surface of the skin. The chamber was cov-

TABLE 11

| | TISSUE FLUORESCENCE | | | | | | | | |
|---|---|---|---|---|---|---|---|---|---|
| | Strateum Corneum | | | Epidermis | | | Dermis | | |
| TIME (HRS): | 1.5 | 3 | 24 | 1.5 | 3 | 24 | 1.5 | 3 | 24 |
| BPD-OA | 2.7 | 2.7 | 3 | 0.5 | 0.7 | 1.2 | 0.7 | 0.7 | 1.7 |
| BPD-OL | 3 | 2.8 | 3 | 1.5 | 1.8 | 2.5 | 1.2 | 1.5 | 2.3 |
| CH-014 | 2.5 | 3 | 3 | 1.2 | 1.8 | 1.4 | 1 | 1 | 1 |
| Phospholipid | 3 | 3 | 3 | 1.2 | 1.8 | 2.2 | 1.2 | 1.3 | 1.6 |

EXAMPLE 19

LED Activation of BPD

Light Emitting Diodes (LEDS) which emit light around 690 nm were used to activate BPD for viral inactivation in blood (red cell concentrates). Treatment of red cell concentrates was as follows.

Red cell concentrates (Adsol) were spiked with 6 logs of Vesicular Stomatitis Virus (VSV) per ml. After incubation with virus, samples were incubated for 60 minutes with BPD at 1 μg/ml or 0.5 μg/ml. The samples were washed twice and placed in red cell storage solution, then exposed to red LED light from each of two sides for 5, 10 or 15 minutes (approximately 7, 14 or 22 Joules/cm$^2$). The samples were assayed for remaining infectious virus by a standard TCID 50 (tissue culture infectious dose) assay. Results showed no recoverable virus in any of the samples that had been treated with both BPD and light.

The advantages of using these LEDs compared to other non-laser light sources are, first of all, increased power output (20-24 mw/cm$^2$) compared to red fluorescent lights (approximately 2 mW/cm$^2$). The LED light used in this example was focused around the optimal wavelength (690 nm) for activation of BPD in blood. Secondly, markedly, the LEDs used in the aforementioned method gave rise to markedly decreased treatment times (5-10 minutes or less, depending on dose of BPD). Previous treatment times to achieve 100% viral inactivation in this system are on the order of 1-2 hours.

Figures 1, 2, 3, 4, 5:
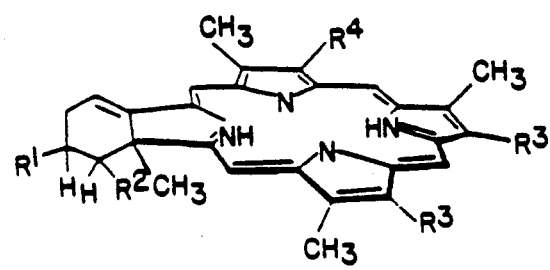
FIGS. 5, 6 and 7 graphically represent the effect of BPD concentration and light exposure times on viral kill in plasma (FIG. 5) and red cell concentrations (FIGS. 5, 6 and 7) in the LED activation study of Example 19.
Figures 1, 2, 3, 4, 5, 6:
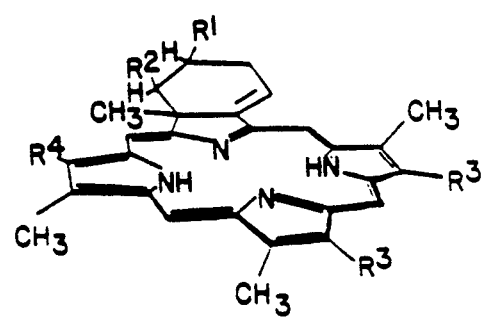
Figures 1, 2:
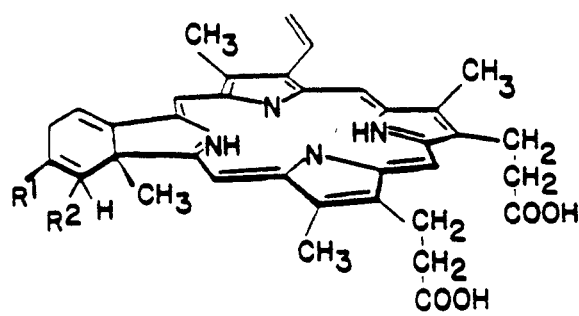
Figure 2:
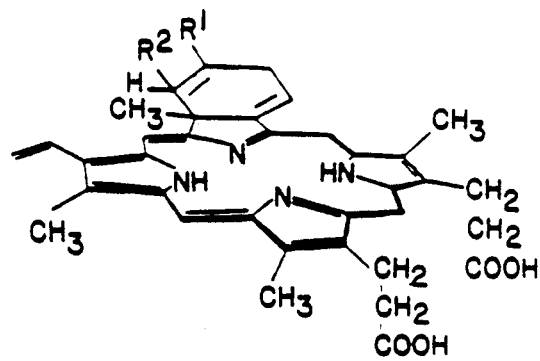
Figures 2, 3:
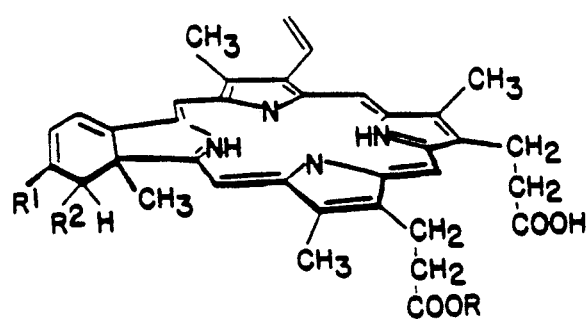
Figures 2, 3, 4:
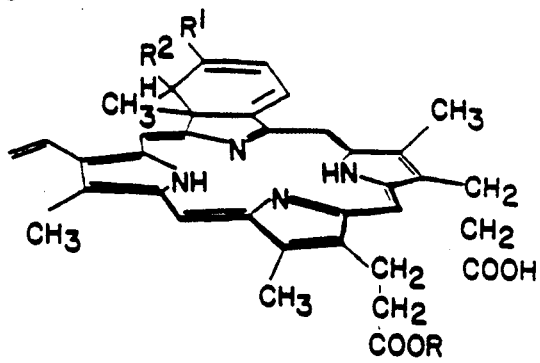
Figure 3:
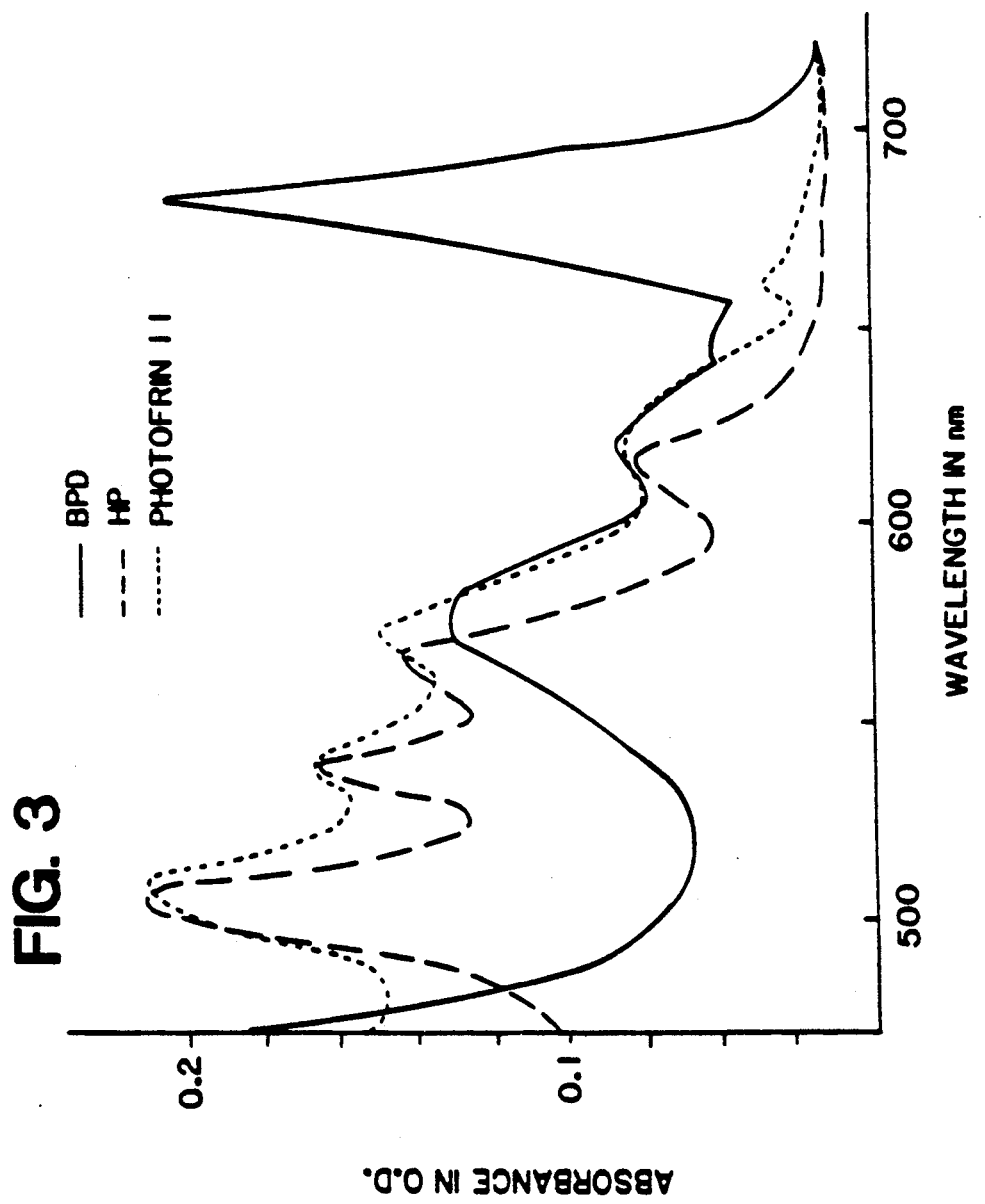
Figure 4:
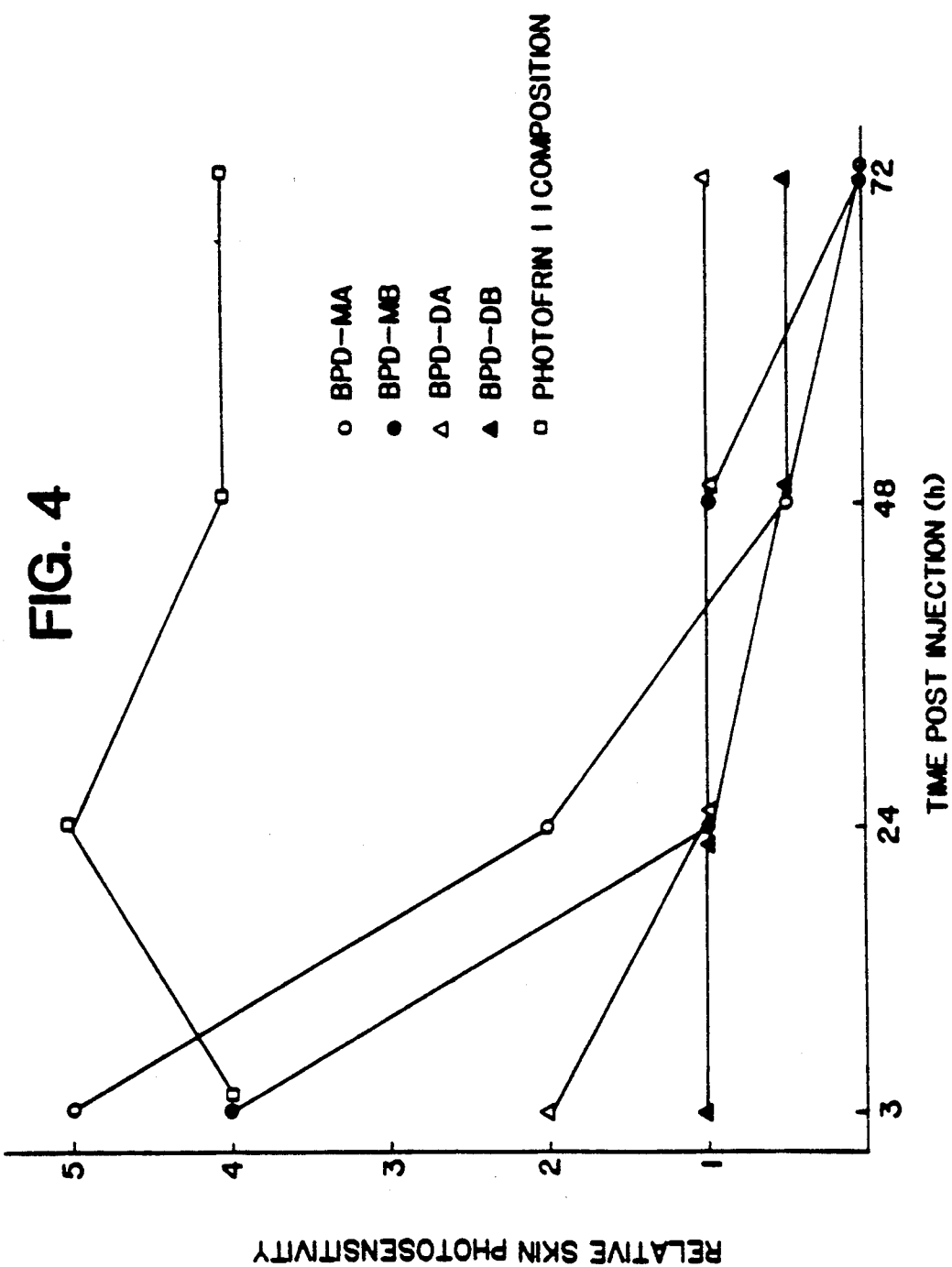
Figure 6:
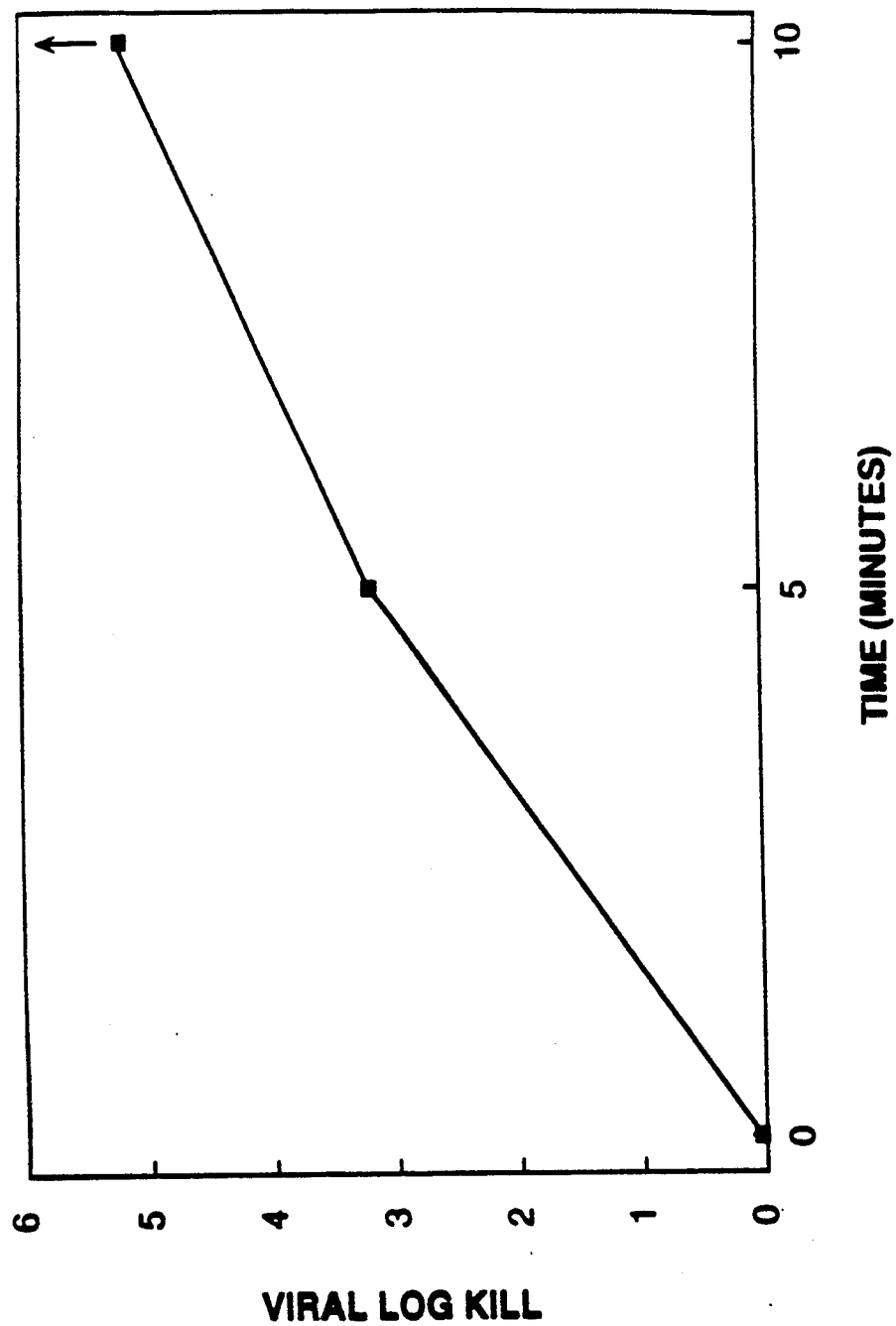
Figure 7:
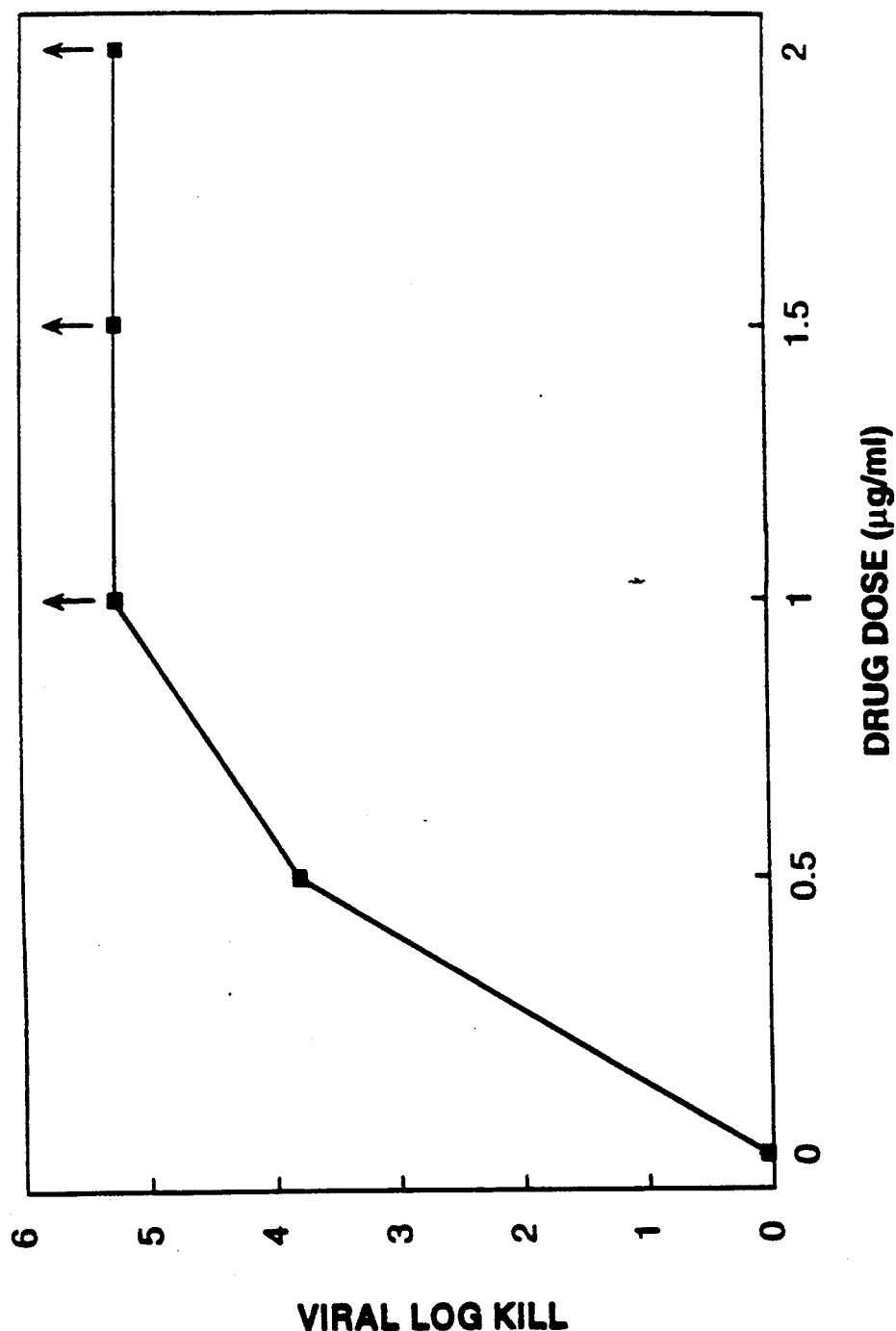

FIGS. 5, 6 and 7 demonstrate results from a variety of experiments to evaluate effects of BPD concentration and light exposure times (light dose) on viral kill in plasma (FIG. 5) or red cell concentrations (FIGS. 5, 6 and 7). A slightly different treatment method was utilized for these studies than that outlined above. In these studies, BPD doses of greater than or equal to 1 μg/ml and light doses of between approximately 6 and 14 Joules/cm$^2$ resulted in 100% viral kill.

Figure 8:
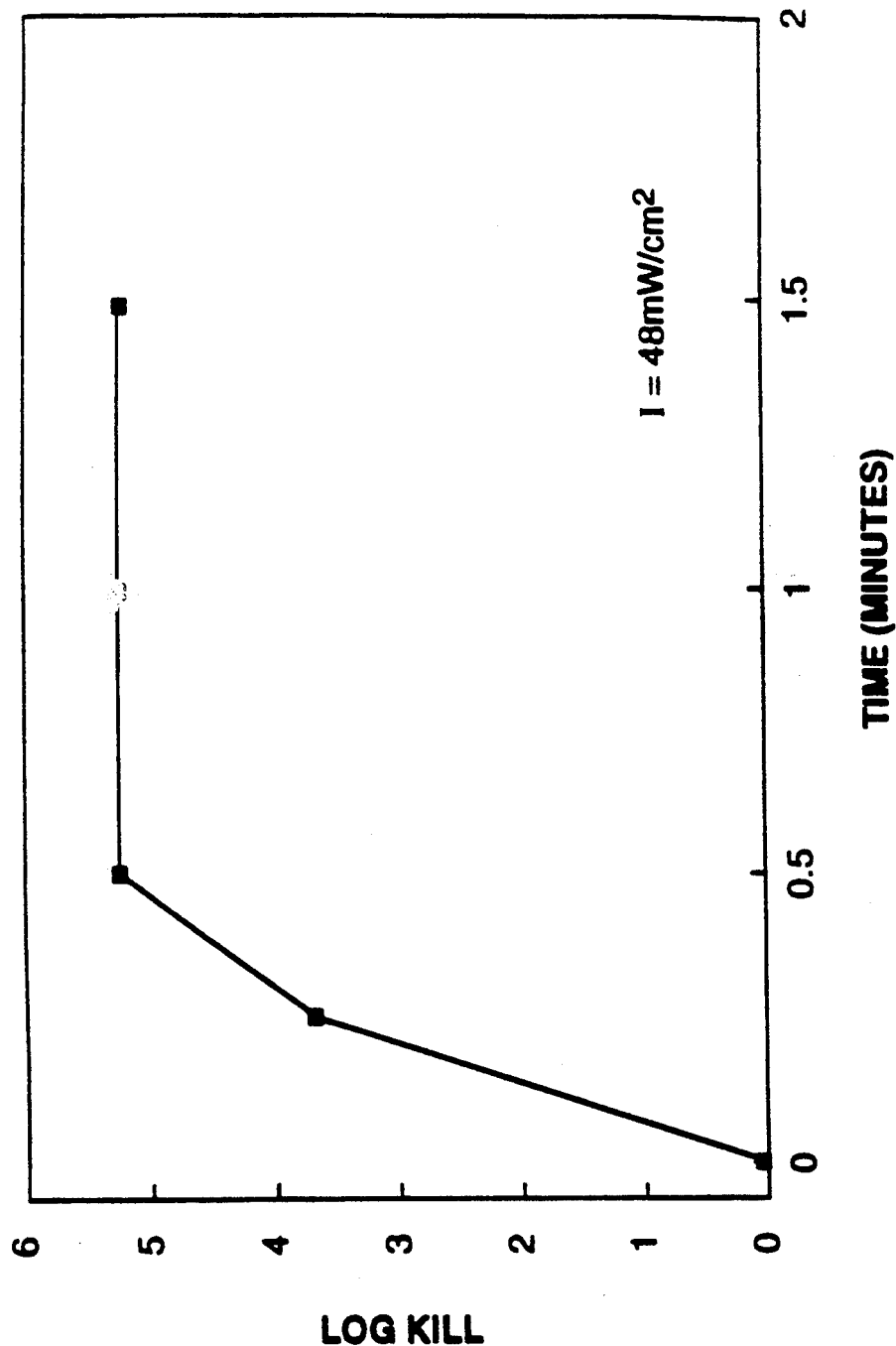
FIGS. 8, 9 and 10 also derive from the LED activation study of Example 19, and demonstrate results achieved with an increase in light intensity.
Figure 9:
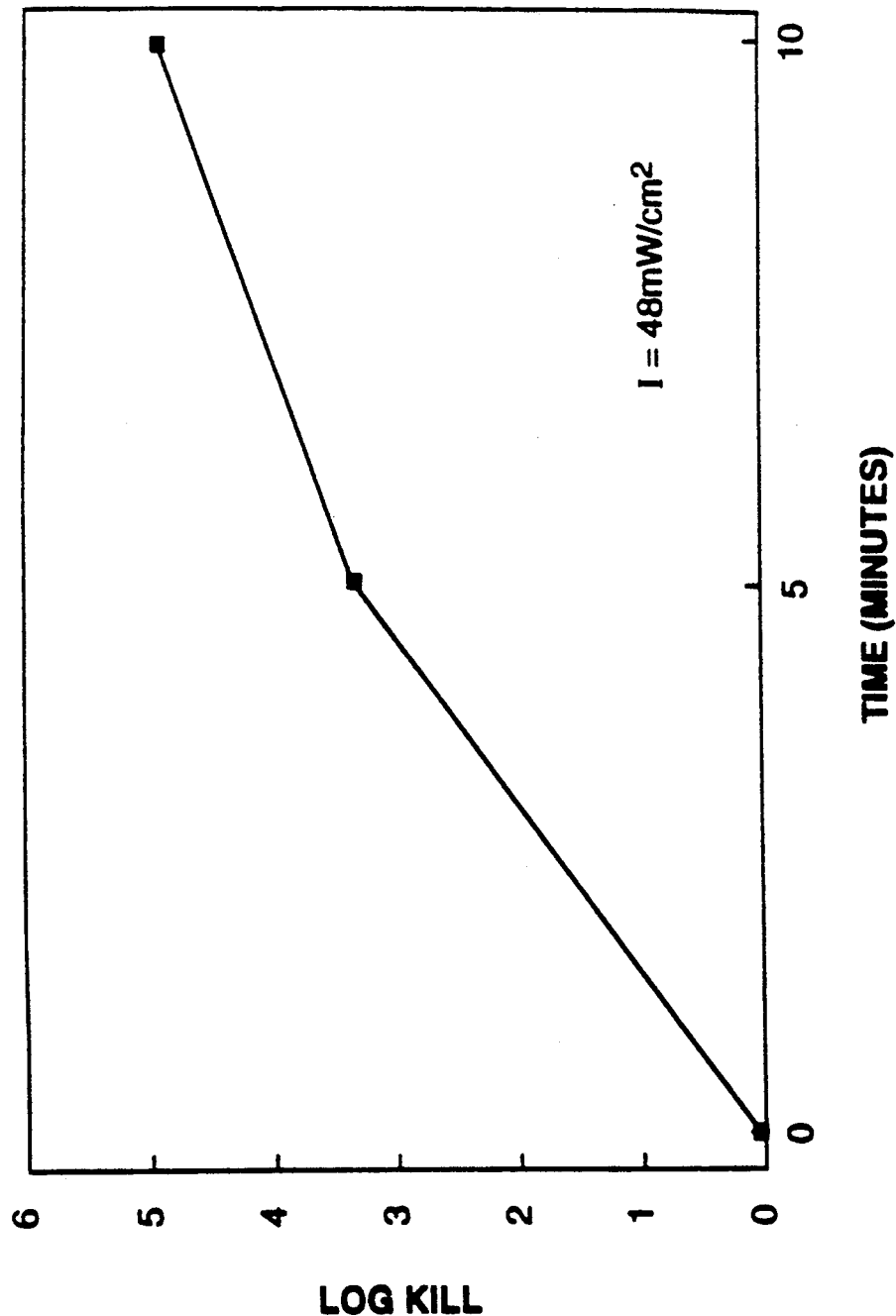
Figure 10:
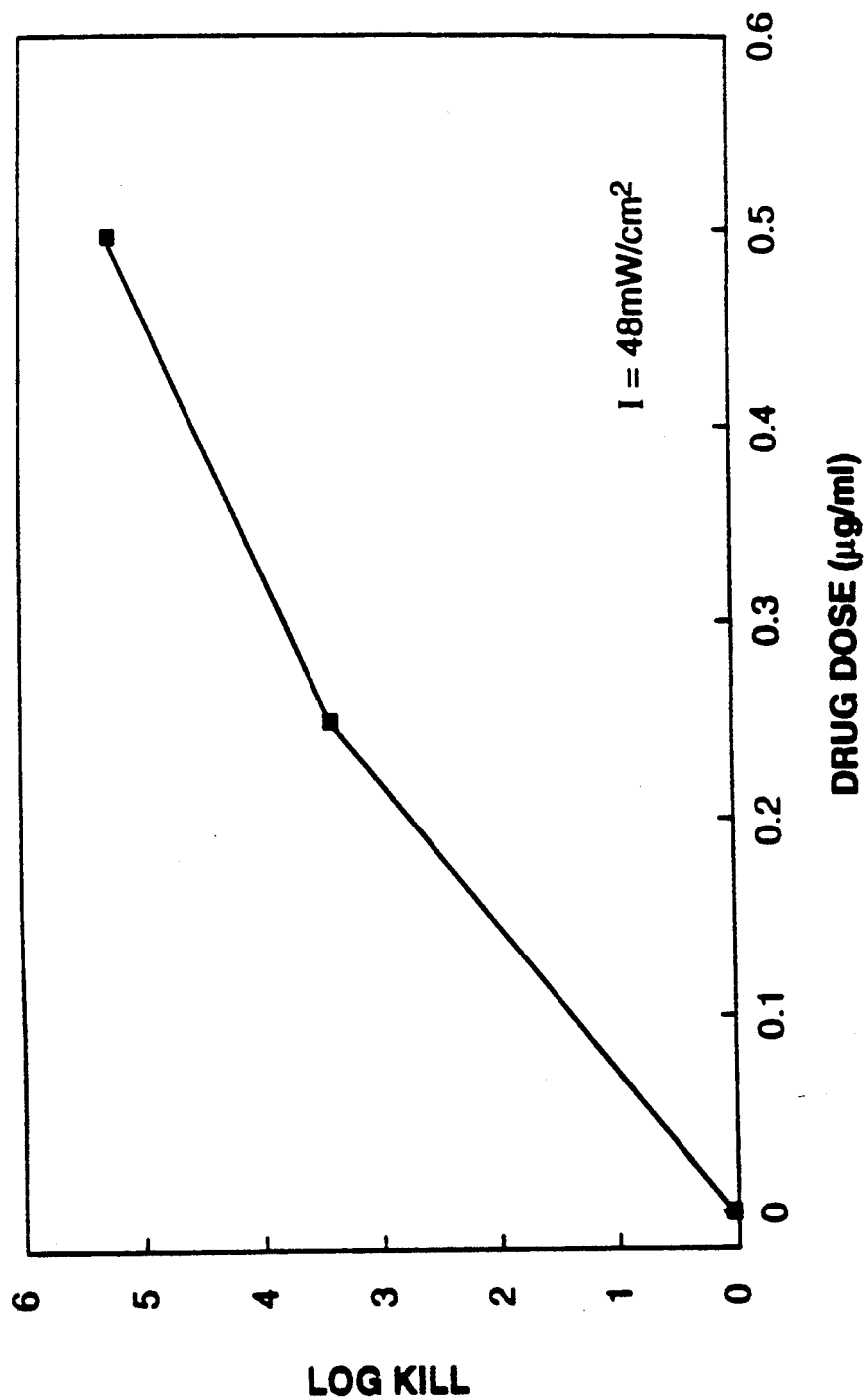

FIGS. 8, 9 and 10 demonstrate results from recent experiments utilizing twice the light intensity (48 mw/cm$^2$) of that utilized in previous studies. These graphs demonstrate that 100% viral kill can be achieved by the use of 0.5 μg BPD/ml and 5 minutes light exposure (approximately 14 Joules/cm$^2$) or 0.25 μg BPD/ml and 10 minutes light exposure (approximately 29 Joules/cm$^2$).

We claim:

1. A method to detect, photosensitize, destroy or impair the functioning of target biological material which comprises contacting said target with an effective amount of a hydro-monobenzoporphyrin (Gp) having a light absorption maximum between 670-780 nm; wherein the Gp is selected from the group consisting of

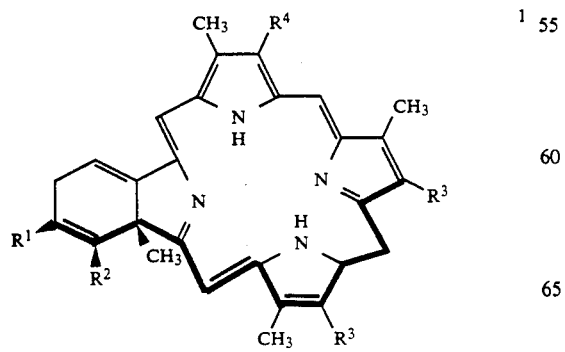

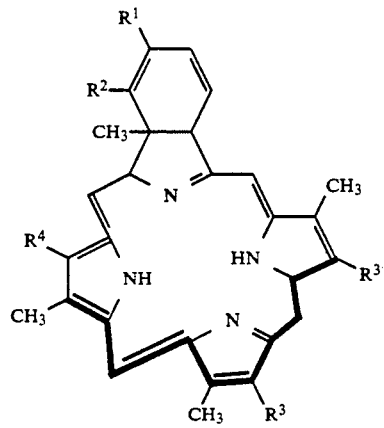

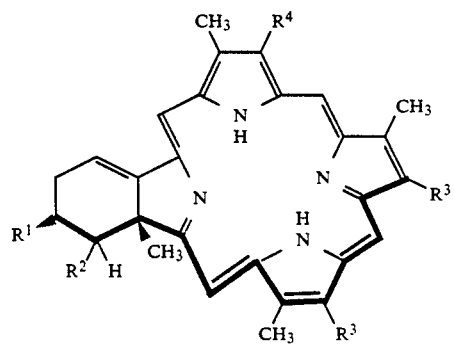

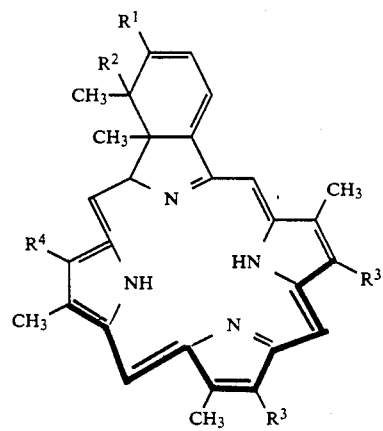

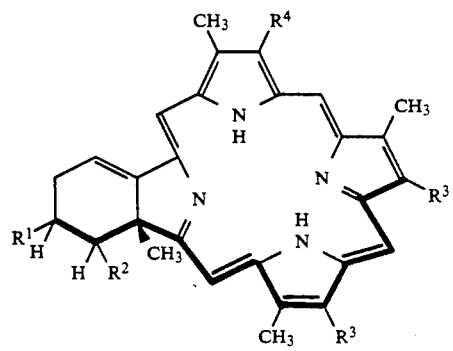

-continued

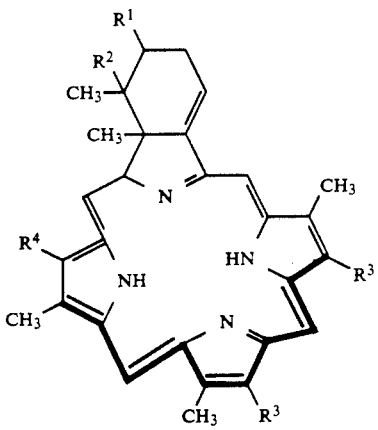

6

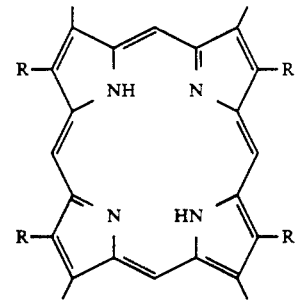

and mixtures thereof and the metalated and labeled forms thereof, wherein each $R^1$ and $R^2$ independently selected from the group consisting of carbalkoxy (2-6C), alkyl (1-6C) sulfonyl, Aryl (6-10C) sulfonyl, aryl (6-10C); cyano; and —$CONR^5CO$— wherein $R^5$ is aryl (6-10C) or alkyl (1-6C)

each $R^3$ is independently carboxyalkyl (2-6C) or a salt, amide, ester or acylhydrazone thereof, or is alkyl (1-6C); and $R^4$ is $CHCH_2$, $CH_2OR^{4'}$, —CHO, —$COOR^4$ $CH(OR^{4'})CH_3$, $CH(OR^{4'})CH_2OR^{4'}$, —$CH(SR^{4'})CH_3$, —$CH(NR^2)CH_3$, —$CH(CN)CH_3$, —$CH(COOR^{4'})CH_3$, —$CH((OOCR^{4'})CH_3$, —CH(halo)CH or —CH(halo)$CH_2$(halo), wherein $R^{4'}$ is H, alkyl (1-6C) optionally substituted with a hydrophilic substituent, or wherein $R^4$ is an organic noninterfering group of <12C resulting from direct or indirect derivatization of vinyl, or wherein $R^4$ consists of 1-3 tetrapyrrole-type nuclei of the formula —L—P wherein —L— is selected from the group consisting of

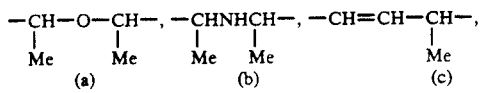

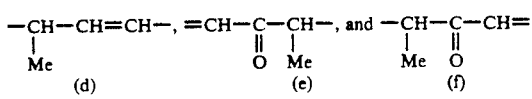

and P is selected from the group consisting of Gp which is of the formula 1-6 but lacking $R^4$ and conjugated through the position shown as occupied by $R^4$ to L, and a porphyrin of the formula:

wherein each R is independently H or lower alkyl (1-4C);

wherein two of the bonds shown as unoccupied on adjacent rings are joined to $R^3$ and one of the remaining bonds shown as unoccupied is joined to $R^4$ and the other to L;

with the proviso that if $R^4$ is $CHCH_2$, both $R^3$ cannot be carbalkoxyethyl;

and irradiating said target with light absorbed by said Gp.

2. The method of claim 1 wherein each $R^3$ is —$CH_2CH_2COOH$ or a salt, amide, ester or acylhydrazone thereof.

3. The method of claim 1 wherein each of $R^1$ and $R^2$ is carbalkoxy (2-6C).

4. The method of claim 2 wherein each of $R^1$ and $R^2$ is carbalkoxy (2-6C).

5. The method of claim 1 wherein the Gp has formula 3 or 4.

6. The method of claim 4 wherein the Gp has formula 3 or 4.

7. The method of claim 1 wherein the Gp has formula 3 or 4 and mixtures thereof, and wherein each $R^1$ and $R^2$ independently selected from the group consisting of carbalkoxy (2-6C), alkyl (1-6C) sulfonyl, aryl (6-10C) sulfonyl, aryl (6-10C) cyano; and —$CONR^5CO$— wherein $R^5$ is aryl (6-10C) or alkyl (1-6C);

each $R^3$ is independently carboxyalkyl (2-6C) or a salt, amide, ester or acylhydrazone thereof, or is alkyl (1-6C);

$R^4$ is $CHCH_2CH_2OR^{4'}$, —CHO, —$COOR^{4'}$, $CH(OR^{4'})CH_3$, $CH(OR^{4'})CH_2OR^{4'}$, —$CH(SR^{4'})CH_3$, —$CH(NR^{4'}_2)CH_3$, —$CH(CN)CH_3$, —$CH(COOR^{4'})CH_3$, —$CH((OOCR^{4'})CH_3$, —CH(halo)$CH_3$, or —CH(halo)$CH_2$(halo), wherein $R^{4'}$ is H, alkyl (1-6C) optionally substituted with a hydrophilic substituent.

8. The method of claim 1 wherein the Gp has formula 3 or 4 and mixtures thereof, and wherein each $R^1$ and $R^2$ is independently selected from the group consisting of carbalkoxy, alkyl (1-6C) sulfonyl, aryl (6-10C) sulfonyl, aryl (6-10C) cyano; and —$CONR^5CO$— wherein $R^5$ is aryl (6-10C) or alkyl (1-6C);

each $R^3$ is independently carboxyalkyl (2-6C) or a salt, amide, ester or acylhydrazone thereof, or is alkyl (1-6C); and wherein $R^4$ is a substituent containing 1-3 tetrapyrrole-type nuclei, of the formula —L—P as herein defined.

9. The method of claim 1 wherein the target materials are cells or tissue harbored in a subject and said contacting comprises administering the Gp in vivo to said subject harboring said cells or tissue.

10. The method of claim 9 wherein the administering is by an oral route.

11. The method of claim 9 wherein the administering is topical.

12. The method of claim 9 wherein the administering is by injection.

13. The method of claim 9 wherein the Gp further contains a label.

14. The method of claim 13 wherein the label is selected from the group consisting of technetium, gallium and indium.

15. The method of claim 1 wherein the target is contained in a biological fluid.

16. The method of claim 15 wherein the biological fluid is blood or blood plasma.

17. The method of claim 16 wherein the fluid is treated ex vivo.

18. The method of claim 1 wherein said method is to photosensitize, destroy or impair the functioning of target biological material, and where said irradiating is conducted with light of wavelength between 670–780 nm.

19. The method of claim 18 wherein said irradiation is supplied by a laser.

20. The method of claim 18 wherein said irradiation is supplied by a light-emitting diode.

21. The method of claim 1 wherein the target material is the lesions of psoriasis.

22. The method of claim 1 wherein the target material is atherosclerotic plaque.

23. The method of claim 1 wherein the target material is a virus.

24. The method of claim 1 which is to detect the target biological material and wherein said irradiating excites said Gp to emit fluorescence.

25. A method to detect or impair the metabolism of or to effect the destruction of target virus, cells, or tissues which comprises contacting said target with an effective amount of the Gp compound as defined in claim 1, or a pharmaceutical composition thereof, and irradiating the contacted virus, cells, or tissues with light absorbed by the Gp.

26. The method of claim 25 wherein the target comprises cells selected from tumor cells, T-suppressor cells and infective cells.

* * * * *

UNITED STATES PATENT AND TRADEMARK OFFICE
CERTIFICATE OF CORRECTION

PATENT NO. : 5,283,255
DATED : February 1, 1994
INVENTOR(S) : Levy et al.

It is certified that error appears in the above-indentified patent and that said Letters Patent is hereby corrected as shown below:

On the title page item:
[60] Division of Ser. No. 718,393, should be --Continuation of Ser. No. 718,393,--.

Signed and Sealed this

Twenty-eighth Day of June, 1994

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO.      : 5,283,255
APPLICATION NO. : 07/943895
DATED           : February 1, 1994
INVENTOR(S)     : Levy et al.

It is certified that error appears in the above-identified patent and that said Letters Patent is hereby corrected as shown below:

Replacement Formal Drawings
Please Delete Figs. 1-1 thur 2-4 and Ring A and B and replace with Figs 1-1 thur 2-4 and Ring A and Ring B

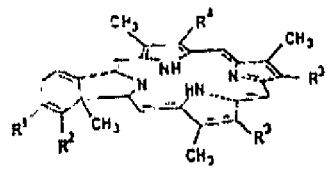

FIG. 1-1

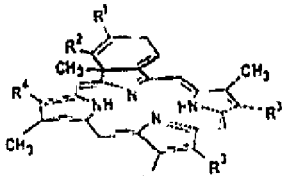

FIG. 1-2

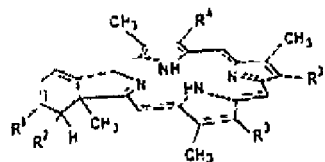

FIG. 1-3

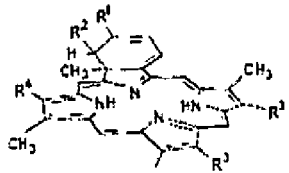

FIG. 1-4

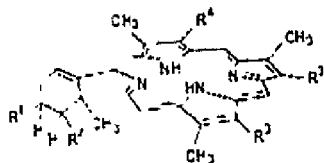

FIG. 1-5

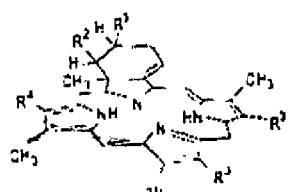

FIG. 1-6

UNITED STATES PATENT AND TRADEMARK OFFICE
CERTIFICATE OF CORRECTION

PATENT NO.         : 5,283,255
APPLICATION NO.    : 07/943895
DATED              : February 1, 1994
INVENTOR(S)        : Levy et al.

It is certified that error appears in the above-identified patent and that said Letters Patent is hereby corrected as shown below:

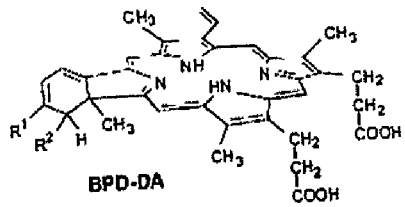

FIG. 2-1

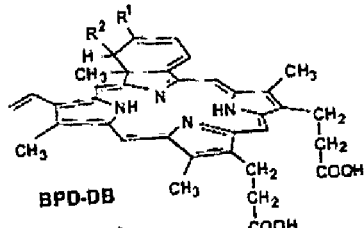

FIG. 2-2

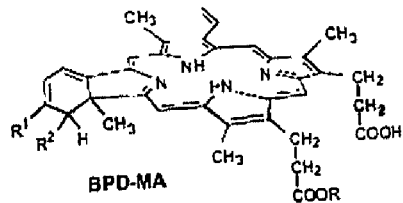

FIG. 2-3

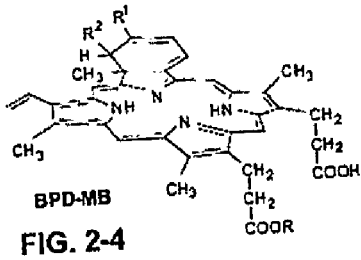

FIG. 2-4

UNITED STATES PATENT AND TRADEMARK OFFICE
CERTIFICATE OF CORRECTION

PATENT NO. : 5,283,255  
APPLICATION NO. : 07/943895  
DATED : February 1, 1994  
INVENTOR(S) : Levy et al.

It is certified that error appears in the above-identified patent and that said Letters Patent is hereby corrected as shown below:

Replacement Drawing, A Ring, Column 28, Lines 55-67

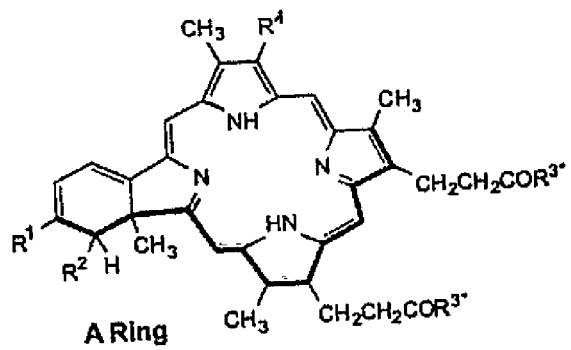

Replacement Drawing, B Ring, Column 29

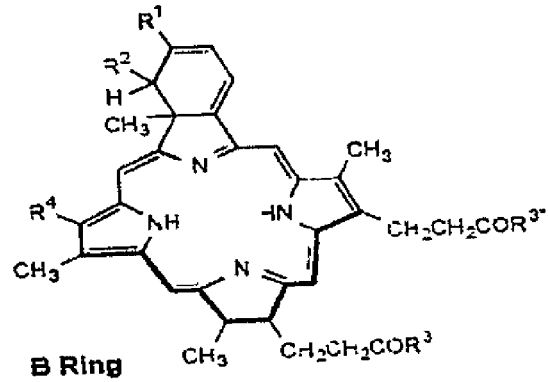

Replacement Drawings, Claim 1, Compound 1, Column 37, Lines 55-65
Please delete compound 1-6 and replace with Compound 1-6

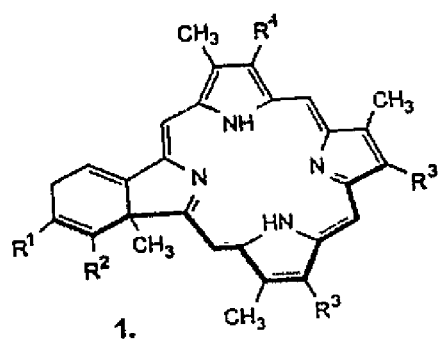

UNITED STATES PATENT AND TRADEMARK OFFICE
CERTIFICATE OF CORRECTION

PATENT NO. : 5,283,255
APPLICATION NO. : 07/943895
DATED : February 1, 1994
INVENTOR(S) : Levy et al.

It is certified that error appears in the above-identified patent and that said Letters Patent is hereby corrected as shown below:

Replacement Drawing Claim 1, Compound 2, Column 38, Lines 3-19

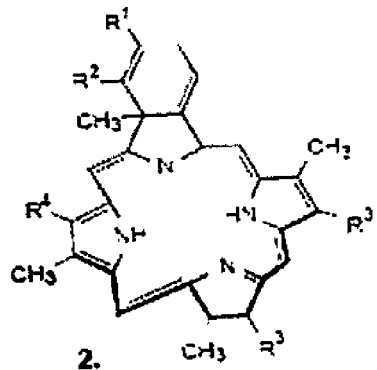

Replacement Drawing, Claim 1, Compound 3, Column 38, Lines 20-34

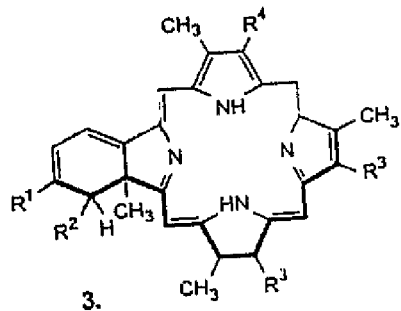

Replacement Drawing, Claim 1, Compound 4, Column 38, Lines 36-51

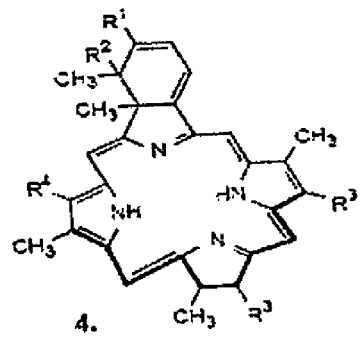

UNITED STATES PATENT AND TRADEMARK OFFICE
CERTIFICATE OF CORRECTION

PATENT NO. : 5,283,255
APPLICATION NO. : 07/943895
DATED : February 1, 1994
INVENTOR(S) : Levy et al.

It is certified that error appears in the above-identified patent and that said Letters Patent is hereby corrected as shown below:

Replacement Drawing, Claim 1, Compound 5, Column 38, Lines 55-65

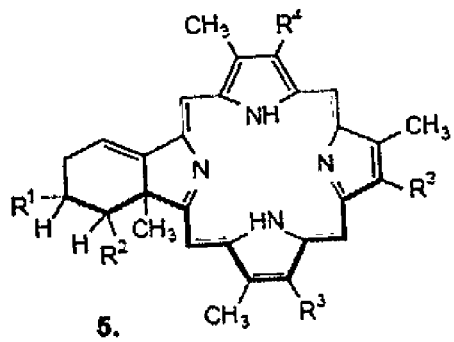

Replacement Drawing, Claim 1, Compound 6, Column 39, Lines 3-19

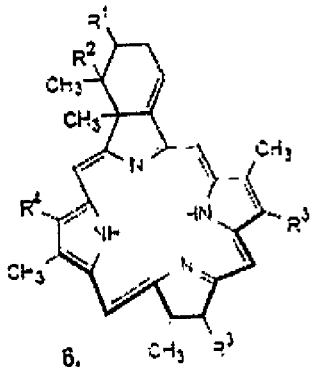

Signed and Sealed this

Twentieth Day of March, 2007

JON W. DUDAS
*Director of the United States Patent and Trademark Office*